United States Patent
Hofmann et al.

(10) Patent No.: US 11,975,988 B2
(45) Date of Patent: May 7, 2024

(54) DETERMINATION OF HYDROXYL RADICAL SCAVENGING CAPACITY AND RELATED TECHNIQUES IN ADVANCED OXIDATIVE PROCESSES

(71) Applicant: THE GOVERNING COUNCIL OF THE UNIVERSITY OF TORONTO, Toronto (CA)

(72) Inventors: Ronald Hofmann, Whitby (CA); Chengjin Wang, Toronto (CA); Erik Rosenfeldt, Ashland, VA (US)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 842 days.

(21) Appl. No.: 16/963,125

(22) PCT Filed: Jan. 17, 2019

(86) PCT No.: PCT/CA2019/050061
§ 371 (c)(1),
(2) Date: Jul. 17, 2020

(87) PCT Pub. No.: WO2019/140524
PCT Pub. Date: Jul. 25, 2019

(65) Prior Publication Data
US 2021/0053841 A1    Feb. 25, 2021

Related U.S. Application Data

(60) Provisional application No. 62/618,667, filed on Jan. 18, 2018.

(51) Int. Cl.
*C02F 1/32* (2023.01)
*C02F 1/00* (2023.01)
(Continued)

(52) U.S. Cl.
CPC ............... *C02F 1/008* (2013.01); *C02F 1/32* (2013.01); *C02F 1/722* (2013.01); *G01N 21/31* (2013.01);
(Continued)

(58) Field of Classification Search
CPC ......... G01N 2021/7783; G01N 21/274; G01N 21/31; G01N 21/85; G01N 2201/127;
(Continued)

(56) References Cited

U.S. PATENT DOCUMENTS 9,594,015 B2    3/2017    Ried et al.

OTHER PUBLICATIONS

Wang, C.; Rosenfeldt E.; Li, Y.; Hofmann, R. (2019). An External Standard Calibration Method to Measure the Hydroxyl Radical Scavenging Capacity of Water Samples. International Ultraviolet Association World Congress & Exhibition. Sydney, Australia. Feb. 13, 2019.

(Continued)

*Primary Examiner* — Terry K Cecil
(74) *Attorney, Agent, or Firm* — Nolte Lackenbach Siegel

(57) ABSTRACT

The determination of hydroxyl radical scavenging capacity of contaminated water can be achieved by developing an external calibration model. The model can be prepared using standard solutions where scavenging capacities are determined, and then the solutions are treated with addition of an oxidant and a dye, followed by UV treatment to form hydroxyl radicals that are scavenged by species in the standard solution. The residual dye content can then be measured using absorbance. The absorbance and the scavenging capacity data for the standard solutions are used to build the model, which can then be implemented to determine scavenging capacity of contaminated water. Water samples can be subjected to the same treatment as the standard solutions, the absorbance of the water sample is (Continued)

then obtained, and then the model is used to determine the corresponding scavenging capacity. Determining scavenger capacity of contaminated water can aid in advanced oxidation processing (AOP).

19 Claims, 11 Drawing Sheets

(51) Int. Cl.
| | | |
|---|---|---|
| *C02F 1/72* | (2023.01) | |
| *G01N 21/31* | (2006.01) | |
| *G01N 21/85* | (2006.01) | |
| *G01N 31/22* | (2006.01) | |
| *G01N 33/18* | (2006.01) | |

(52) U.S. Cl.
CPC .............. *G01N 21/85* (2013.01); *G01N 31/22* (2013.01); *G01N 33/1893* (2013.01); *C02F 2305/023* (2013.01); *G01N 2201/127* (2013.01)

(58) Field of Classification Search
CPC .... G01N 31/22; G01N 33/1893; C02F 1/008; C02F 1/32; C02F 1/722; C02F 1/78; C02F 2305/023
See application file for complete search history.

(56) References Cited

OTHER PUBLICATIONS

Wang, C.; Rosenfeldt, E.; Li, Y.; Hofmann, R. (2020). External Standard Calibration Method to Measure the Hydroxyl Radical Scavenging Capacity of Water Samples. Environmental Science & Technology. 54 (3), 1929-1937.

Rosenfeldt, Erik J., and Karl G. Linden. (2007). The ROH, UV concept to characterize and the model UV/H2O2 process in natural waters. Environmental science & technology 41 (7): 2548-2553.

Li, M.; Huang, Y.; Sun, Z.; Zhang, Y.; Bolton, J.; Qiang, Z. Prediction of micro-pollutant degradation by UV/H2O2 in water by the combination of model simulation and portable measurements; pp. 17-51.

DETERMINATION OF HYDROXYL RADICAL SCAVENGING CAPACITY AND RELATED TECHNIQUES IN ADVANCED OXIDATIVE PROCESSES

CROSS REFERENCE TO RELATED APPLICATION

This application is a U.S. National Stage Patent Application based on PCT No. PCT/CA2019/050061, filed Jan. 17, 2019, claiming priority to U.S. Application No. 62/618,667, filed on Jan. 18, 2018, the entire contents of which are hereby incorporated by reference as though fully set forth herein.

TECHNICAL FIELD

The technical field generally relates to advanced oxidation processes (AOP) of aqueous streams and more particularly to methods including the determination of hydroxyl radical scavenging capacity of contaminated water and adapting AOP treatments accordingly.

BACKGROUND

Advanced oxidation processes (AOP) can include the treatment of contaminated water using ultraviolet (UV) and hydrogen peroxide, for example. During such AOP treatments, hydroxyl radicals are formed and react with various contaminant species in the contaminated water and are thus consumed. It can be relatively challenging to determine the capacity of a given contaminated water stream for scavenging hydroxyl radicals. For example, attempting to determine the composition of the contaminated water in order to estimate hydroxyl radical scavenging capacity based on the concentrations of the different constituents has various drawbacks. As contaminated waters that are treated using AOP are often complex multi-component systems that vary in composition over time, it can be challenging to efficiently provide a controlled hydrogen peroxide and/or UV dosage based on the contents of the contaminated water. There is indeed a need for a technology that overcomes at least some of the difficulties related to determining hydroxyl radical scavenging capacity, particularly in the context of AOP.

SUMMARY

Developing and implementing an external calibration model for determining radical scavenging capacity of contaminated water can enhance AOP operations.

In some implementations, the external calibration model can be prepared using standard solutions (e.g., comprising water and an alcohol). The scavenging capacities of the standard solutions are determined, and then the standard solutions are subjected to a test oxidation treatment, which can involve the addition of an oxidant (e.g., hydrogen peroxide), a dye (e.g., methylene blue), followed preferably by an ultraviolet (UV) treatment to form hydroxyl radicals that are scavenged by species in the standard solution to form a treated solution. The residual dye content is then measured for the various treated solutions, preferably by determining absorbance at the signature wavelength of the dye. The absorbance data and the scavenging capacity data for the standard solutions can then be used to build the external calibration model, for example by plotting a scavenging capacity versus absorbance curve. In addition, an additional absorbance measurement can be taken before the oxidation treatment (e.g., before the UV treatment) and then the difference between the two absorbance measurements can be used in the external calibration model (e.g., scavenging capacity versus $1/\Delta_{ln(absorbance)}$ or another relationship).

In some alternative implementations, the oxidation treatment is performed to achieve a target dye degradation level (e.g., 20% degradation) and the reaction time to achieve that degradation level is determined and used to build the external calibration model, for example by plotting a scavenging capacity versus time (to achieve the target degradation) curve.

In some implementations, there is provided a process for treating contaminated water using an advanced oxidation process (AOP) that includes addition of hydrogen peroxide and ultraviolet (UV) treatment to generate hydroxyl radicals, the process comprising:
  withdrawing a slipstream of the contaminated water upstream of the addition of the hydrogen peroxide and the UV treatment;
  determining hydroxyl radical scavenging capacity of the slipstream, comprising:
    adding hydrogen peroxide and a dye to the slipstream;
    subjecting the slipstream to a UV treatment to generate hydroxyl radicals that react with contaminants and the dye in the slipstream, to produce a treated slipstream;
    determining absorbance of the treated slipstream at a signature wavelength of the dye to obtain an absorbance measurement; and
    converting the absorbance measurement to hydroxyl radical scavenging capacity via a pre-determined external calibration model and thereby determining the hydroxyl radical scavenging capacity of the contaminated water from which the slipstream was withdrawn, wherein the external calibration model has been developed by:
      preparing multiple standard solutions comprising water and an alcohol scavenger compound at different concentrations;
      determining respective hydroxyl radical scavenging capacities of the standard solutions;
      adding to each standard solution hydrogen peroxide and a dye of the same type as added to the slipstream;
      subjecting each standard solution to UV treatment to generate hydroxyl radicals that react with the dye and the alcohol scavenger compound, to partially degrade the dye such that the resulting treated standard solution has a corresponding residual dye content; and
      determining absorbance at the signature wavelength of the dye of each treated standard solution to obtain a corresponding absorbance measurement, and to thereby obtain a relation between hydroxyl radical scavenging capacity and the absorbance measurement to provide the external calibration model; and
  controlling the AOP based on the determined hydroxyl radical scavenging capacity of the contaminated water.

The contaminated water can be contaminated drinking water. The dye can be methylene blue (MB). The MB can be provided at an MB concentration between 1 µM and 10 µM in the slipstream and in the standard solutions. The alcohol scavenger compound can be isopropyl alcohol (IPA), and the IPA can be provided in IPA concentrations between 0 µM and 120 µM in the standard solutions. The alcohol scavenger compound can alternatively be tert butyl alcohol (TBA).

The UV treatment can include subjecting the standard solutions and the slipstream to a fixed UV intensity over a fixed time. The UV treatment can include providing a plug flow of the slipstream that includes the hydrogen peroxide and the dye through a UV-transparent pipe within a UV cell, and exposing the plug flow to UV light at the fixed UV intensity over a fixed time while travelling through the UV-transparent pipe.

The external calibration model can include a calibration curve of $1/\Delta_{ln(absorbance)}$ versus scavenging capacity where absorbance readings are taken before and after the UV treatment; absorbance versus scavenging capacity; 1/absorbance versus scavenging capacity; or $\Delta$absorbance versus scavenging capacity where absorbance readings are taken before and after the UV treatment.

The steps of withdrawing the slipstream, determining the hydroxyl radical scavenging capacity of the slipstream, and controlling the AOP can be performed continuously, in batch mode or semi-batch mode.

In some implementations, there is provided a process for treating contaminated water using an advanced oxidation process (AOP) that includes addition of a primary oxidant or oxidant generator and ultraviolet (UV) treatment to generate hydroxyl radicals, the process comprising:

obtaining a sample of the contaminated water upstream of the addition of the primary oxidant and the UV treatment;

determining hydroxyl radical scavenging capacity of the sample, comprising:

adding an oxidant and an indicator to the sample;

subjecting the sample to a UV treatment to generate hydroxyl radicals that react with contaminants and the indicator in the sample, to produce a treated sample;

determining a residual indicator content parameter of the treated sample; and converting the residual indicator content parameter to hydroxyl radical scavenging capacity via a predetermined external calibration model and thereby determining the hydroxyl radical scavenging capacity of the contaminated water from which the sample was obtained, wherein the external calibration model has been developed by:

preparing multiple standard solutions comprising water and a standard scavenger compound at different concentrations;

determining respective hydroxyl radical scavenging capacities of the standard solutions;

adding to each standard solution an oxidant of the same type as added to the sample, and an indicator of the same type as added to the sample;

subjecting each standard solution to UV treatment to generate hydroxyl radicals that react with the indicator and the standard scavenger compound to partially degrade the indicator such that the resulting treated standard solution has a corresponding residual indicator content; and determining a residual indicator content parameter of each treated standard solution, to thereby obtain a relation between hydroxyl radical scavenging capacity and the residual indicator content to provide the external calibration model; and controlling the AOP based on the determined hydroxyl radical scavenging capacity of the contaminated water.

The sample of the contaminated water can be a slipstream. The primary oxidant of the AOP can be hydrogen peroxide or ozone. The oxidant generator of the AOP can be $TiO_2$. The oxidant in the step of determining the hydroxyl radical scavenging capacity of the sample and the standard solutions, can be hydrogen peroxide. The oxidant in the step of determining the hydroxyl radical scavenging capacity of the sample and the standard solutions, can also be added at a concentration between 10 mg/L and 50 mg/L. The Indicator can be a dye, such as methylene blue (MB). The MB can be provided at an MB concentration between 1 µM and 10 µM in the sample and in the standard solutions.

The steps of determining the residual indicator content parameter of the treated sample and determining the residual indicator content parameter of the corresponding standard solutions, can include determining absorbance at the signature wavelength of the dye, to obtain a relation between hydroxyl radical scavenging capacity and the absorbance measurement to provide the external calibration model.

The contaminated water can be contaminated drinking water, or other types of water.

The standard scavenger compound can be an alcohol scavenger compound. The alcohol scavenger compound can be isopropyl alcohol (IPA), and the IPA can be provided in IPA concentrations between 0 µM and 120 µM in the standard solutions. The alcohol scavenger compound can alternatively be tert butyl alcohol (TBA).

The UV treatment can include subjecting the standard solutions and the slipstream to a fixed UV intensity over a fixed time. The UV treatment can include providing a plug flow of the sample that includes the hydrogen peroxide and the dye through a UV-transparent pipe within a UV cell, and exposing the plug flow to UV light at the fixed UV intensity over a fixed time while travelling through the UV-transparent pipe.

The external calibration model can include a calibration curve of $1/\Delta_{ln(absorbance)}$ versus scavenging capacity where absorbance readings are taken before and after the UV treatment; absorbance versus scavenging capacity; 1/absorbance versus scavenging capacity; or $\Delta$absorbance versus scavenging capacity where absorbance readings are taken before and after the UV treatment.

The steps of obtaining the sample, determining the hydroxyl radical scavenging capacity of the sample, and controlling the AOP can be performed continuously, in batch mode or semi-batch mode.

In some implementations, there is provided a method for treating contaminated water using an advanced oxidation process (AOP), comprising obtaining a sample of the contaminated water upstream of the AOP; determining hydroxyl radical scavenging capacity of the sample of the contaminated water using an external calibration model; providing feedforward control of the AOP based on the determined hydroxyl radical scavenging capacity of the contaminated water.

The contaminated water can be contaminated drinking water. The sample of the contaminated water can be a slipstream. The AOP can include addition of a primary oxidant and UV treatment, where the primary oxidant can be hydrogen peroxide or ozone for example. The AOP can include the addition of an oxidant generator and UV treatment, and the oxidant generator can be $TiO_2$.

The step of determining hydroxyl radical scavenging capacity of the sample can include performing a monitoring protocol on the sample, wherein the monitoring protocol is substantially the same as a calibration protocol performed on standard solutions to develop the external calibration model.

The monitoring protocol can include adding an indicator to the sample; subjecting the sample to an oxidation process to generate hydroxyl radicals that react with contaminants and the indicator in the sample, to produce a treated sample; determining a residual indicator content parameter of the treated sample; and converting the residual indicator content parameter to hydroxyl radical scavenging capacity via the external calibration model and thereby determining the hydroxyl radical scavenging capacity of the contaminated water from which the sample was obtained.

The calibration protocol can include preparing multiple standard solutions comprising water and a standard scavenger compound at different concentrations; determining respective hydroxyl radical scavenging capacities of the standard solutions; adding to each standard solution an indicator of the same type as added to the sample; subjecting each standard solution to an oxidation process at the same conditions as the sample, to generate hydroxyl radicals that react with the indicator and the standard scavenger compound to partially degrade the indicator such that the resulting treated standard solution has a corresponding residual indicator content; and determining a residual indicator content parameter of each treated standard solution, to thereby obtain a relation between hydroxyl radical scavenging capacity and the residual indicator content to provide the external calibration model.

The oxidation process can be a hydrogen peroxide and UV treatment process, and wherein hydrogen peroxide ma be added to each standard solution prior to corresponding UV treatment. Alternatively, in some cases, the oxidation process can be a non-UV based oxidation process.

The monitoring protocol can include adding an oxidant and an indicator to the sample; subjecting the sample to a UV treatment to generate hydroxyl radicals that react with contaminants and the indicator in the sample, to produce a treated sample; determining a residual indicator content parameter of the treated sample; and converting the residual indicator content parameter to hydroxyl radical scavenging capacity via the external calibration model and thereby determining the hydroxyl radical scavenging capacity of the contaminated water from which the sample was obtained.

The calibration protocol can include preparing multiple standard solutions comprising water and a standard scavenger compound at different concentrations; determining respective hydroxyl radical scavenging capacities of the standard solutions; adding to each standard solution an oxidant of the same type as added to the sample, and an indicator of the same type as added to the sample; subjecting each standard solution to UV treatment to generate hydroxyl radicals that react with the indicator and the standard scavenger compound to partially degrade the indicator such that the resulting treated standard solution has a corresponding residual indicator content; and determining a residual indicator content parameter of each treated standard solution, to thereby obtain a relation between hydroxyl radical scavenging capacity and the residual indicator content to provide the external calibration model.

Optionally, the oxidant is hydrogen peroxide, and the hydrogen peroxide is added at a concentration between 10 mg/L and 50 mg/L. The indicator can be a dye, such as methylene blue (MB). The dye can be provided at a dye concentration between 1 $\mu M$ and 10 $\mu M$. The standard scavenger compound can be an alcohol scavenger compound, such as isopropyl alcohol (IPA) which can be provided in IPA concentrations between 0 $\mu M$ and 120 $\mu M$ in the standard solutions. The alcohol scavenger compound can also be tert butyl alcohol (TBA).

The UV treatment can include subjecting the standard solutions and the slipstream to a fixed UV intensity over a fixed time. The UV treatment can include providing a plug flow of the sample that includes the hydrogen peroxide and the dye through a UV-transparent pipe within a UV cell, and exposing the plug flow to UV light at the fixed UV intensity over a fixed time while travelling through the UV-transparent pipe.

The external calibration model can include a calibration curve of $1/\Delta_{ln(absorbance)}$ versus scavenging capacity where absorbance readings are taken before and after the UV treatment; absorbance versus scavenging capacity; 1/absorbance versus scavenging capacity; or $\Delta$absorbance versus scavenging capacity where absorbance readings are taken before and after the UV treatment.

The steps of obtaining the sample, determining the hydroxyl radical scavenging capacity of the sample, and providing feedforward control of the AOP can be performed continuously or in batch mode or semi-batch mode.

The monitoring protocol can include adding an indicator to the sample; subjecting the sample to an oxidation process to generate hydroxyl radicals that react with contaminants and the indicator in the sample, to produce a treated sample having a target residual indicator content parameter; determining reaction time of the oxidation process to achieve the target residual indicator content parameter; and converting the reaction time to hydroxyl radical scavenging capacity via the external calibration model and thereby determining the hydroxyl radical scavenging capacity of the contaminated water from which the sample was obtained. The calibration protocol can include preparing multiple standard solutions comprising water and a standard scavenger compound at different concentrations; determining respective hydroxyl radical scavenging capacities of the standard solutions; adding to each standard solution an indicator of the same type as added to the sample; subjecting each standard solution to an oxidation process at the same conditions as the sample, to generate hydroxyl radicals that react with the indicator and the standard scavenger compound to partially degrade the indicator to a target residual indicator content parameter, such that the resulting treated standard solution has a corresponding reaction time of the oxidation process to achieve the target residual indicator content parameter; and determining the reaction time for each treated standard solution to achieve the target residual indicator content parameter, to thereby obtain a relation between hydroxyl radical scavenging capacity and the reaction time to provide the external calibration model.

The oxidation process of the monitoring protocol and the calibration protocol can also be vacuum UV AOP.

In some implementations, there is provided a method for generating a calibration model for determining hydroxyl radical scavenging capacity of contaminated water, the method comprising preparing standard sample solutions comprising water and different concentrations of at least one standard scavenger compound; determining hydroxyl radical scavenging capacity of each of the standard sample solutions; adding an indicator to each standard sample solution; subjecting each of the standard sample solutions to an oxidation process to generate hydroxyl radicals that react with the indicator and the at least one standard scavenger compound, to partially degrade the indicator and produce a corresponding treated standard solution; determining at least one calibration parameter for each the treated standard solution; building the calibration model based on the calibration parameters and the previously determined hydroxyl radical scavenging capacities of the respective standard sample solutions.

The standard scavenger compound can include a single scavenger compound that is an alcohol scavenger compound. The alcohol scavenger compound can be isopropyl alcohol (IPA), which can be provided in IPA concentrations between 0 µM and 120 µM in the standard solutions. The alcohol scavenger compound can alternatively be tert butyl alcohol (TBA). The indicator can include a dye, such as methylene blue (MB), and the dye can be provided at a dye concentration between 1 µM and 10 µM.

The oxidation process can be a primary oxidant and UV treatment process, wherein the primary oxidant is added to each standard solution prior to the corresponding UV treatment. The primary oxidant can be hydrogen peroxide, which may be added at a concentration between 10 mg/L and 50 mg/L. The oxidation process can include vacuum UV oxidation.

The indicator can be partially degraded to between about 1% and about 40%, between about 2% and about 35%, between about 3% and about 30%, between about 4% and about 25%, or between about 5% and about 20%; and/or the indicator can be partially degraded within indicator degradation range between 5% and 25% or between 10% and 20%; and/or the indicator can be partially degraded to a maximum degradation percentage of approximately 50%, 40%, 35%, 30%, 25%, 20%, or 15%. 15% to about 25%.

The calibration parameter can include a residual indicator content parameter. The calibration parameter can also include a residual dye content parameter comprising an absorbance measurement at a signature wavelength of the indicator; and the determining of the parameter in each of the treated standard solutions can include absorbance detection.

The calibration parameter can include a reaction time to achieve a target residual indicator content parameter. The target residual indicator content parameter can include an indicator degradation level that is pre-determined at a value between about 5% to about 40%, 10% to 30% or 15% to 25%.

The water in the standard solutions can be purified or distilled water. The standard solutions are preferably provided to avoid containing a contaminated water component derived from a stream to be treated in an advanced oxidation process (AOP) operation.

The UV treatment can be performed in a UV cell comprising a UV light source and a sample holder. The UV light source can include alight emitting diodes (LEDs). The sample holder can include a UV-transparent pipe for transporting a plug flow of each standard sample solution while the same receives the UV light.

The calibration model is preferably developed for use in controlling an advanced oxidation process (AOP). The AOP can be for treating drinking water, tap water for industrial processing purposes, waste water, leachate, contaminated surface water, and/or groundwater. The AOP can include the addition of a primary oxidant and UV treatment, and the primary oxidant can include or be hydrogen peroxide or ozone. The AOP can include the addition of an oxidant generator and UV treatment, and the oxidant generator can be $TiO_2$.

In some implementations, there is provided a system for monitoring hydroxyl radical scavenging capacity in a contaminated water stream, the system comprising:

a sample supply line configured to receive a flow of standard solutions comprising a standard scavenger compound in a calibration mode, and to receive a flow of a sample of contaminated water in a monitoring mode;

a dye addition line coupled to the sample supply line to add a dye to the flow of each standard solution in the calibration mode, and to the flow of the sample in the monitoring mode;

an ultraviolet (UV) treatment unit comprising:
    a UV treatment cell comprising:
        a UV light source; and
        a region in spaced-apart relation to the UV light source for accommodating a UV-transparent treatment section of the sample supply line that receives UV light from the UV light source in the calibration mode and the monitoring mode, the UV-transparent treatment section transmitting:
            a standard solution mixture comprising a corresponding standard solution and the dye in the calibration mode, wherein the UV light causes formation of hydroxyl radicals that react with the standard scavenger compound and the dye to form a corresponding treated standard solution; and
            a sample mixture comprising the sample of the contaminated water and the dye in the monitoring mode, wherein the UV light causes formation of hydroxyl radicals that react with contaminants and the dye to form a corresponding treated sample; and
    a detector configured to detect a dye content parameter in each treated standard solution in the calibration mode, and to detect a dye content parameter in the treated sample in the monitoring mode.

The system can also include an oxidant addition line coupled to the sample supply line to add an oxidant to the flow of each standard solution in the calibration mode, and to the flow of the sample in the monitoring mode. The system can include pumps for causing fluids in the system to flow. The UV light source can include a light emitting diodes (LEDs) or a mercury UV lamp. The UV-transparent treatment section can be configured horizontally or vertically. The UV-transparent treatment section can be configured to provide a single pass through the UV cell or multiple passes back and forth through the UV vessel. The UV-transparent treatment section can be generally cylindrical in cross-section. The detector can include an absorbance measurement device for measuring absorbance as the dye content parameter.

The system can also include a conversion module configured to receive the dye content parameter, convert the dye content parameter into a calibration parameter that is used in the external calibration model. The external calibration model can include a calibration curve of $1/\Delta_{ln(absorbance)}$ versus scavenging capacity where absorbance readings are taken before and after the UV treatment; absorbance versus scavenging capacity; 1/absorbance versus scavenging capacity; or $\Delta$absorbance versus scavenging capacity where absorbance readings are taken before and after the UV treatment.

The dye content parameter can be absorbance and the calibration parameter can be $1/\Delta_{ln(absorbance)}$, such that the external calibration model comprises a curve of $1/\Delta_{ln(absorbance)}$ versus scavenging capacity; or wherein the external calibration model comprises a curve of $1/\Delta_{ln(dye\ content\ parameter)}$ versus scavenging capacity, 1/dye content parameter versus scavenging capacity, $\Delta$dye content parameter versus scavenging capacity, or dye content parameter versus scavenging capacity.

The system can also include control module configured to receive absorption readings from the detector, converting the absorption reading to a hydroxyl radical scavenging capacity value based on the external calibration model, and coupled to the AOP in order to control a primary oxidant addition unit and/or a UV treatment unit in an AOP treatment plant to adjust primary oxidant dosage and/or UV dosage in accordance with the hydroxyl radical scavenging capacity value.

The system can also include a supplementary detector located and configured for detecting a property of each standard solution prior to the oxidation process. The supplementary detector can be a supplementary absorbance measurement device and the detector is an absorbance measurement device. The supplementary absorbance measurement device can be configured to obtain absorbance readings at the signature wavelength of the indicator when the contaminated water sample has inherent absorption at the signature wavelength of the indicator, and the change in absorbance can be used to determine the calibration parameter.

In some implementations, there is provided an advanced oxidation process (AOP) controller, comprising:
- a receiver module adapted to receive absorption readings from a contaminated water monitoring system;
- a data storage module comprising a pre-determined external calibration model of hydroxyl radical scavenging capacity versus absorption;
- a processing module configured for:
  - receiving each absorption reading from the receiver module;
  - converting the absorption reading to a hydroxyl radical scavenging capacity value based on the external calibration model in the data storage module; and
  - outputting the hydroxyl radical scavenging capacity value; and
- a controller module adapted to receive the hydroxyl radical scavenging capacity value from the processing module, and operatively couplable to a primary oxidant addition unit and/or a UV treatment unit of an AOP treatment system to adjust primary oxidant dosage and/or UV dosage in accordance with the hydroxyl radical scavenging capacity value.

In some implementations, there is provided method for treating contaminated water using an advanced oxidation process (AOP), comprising obtaining a water sample from an AOP operation; determining hydroxyl radical scavenging capacity of the sample of the contaminated water using an external calibration model; and controlling at least one unit operation of the AOP based on the determined hydroxyl radical scavenging capacity of the water sample. Such a method can include one or more features as defined in any one of the previous or subsequent sections.

Optionally, the determining of the hydroxyl radical scavenging capacity of the water sample comprises performing a monitoring protocol on the sample, wherein the monitoring protocol is substantially the same as a calibration protocol performed on standard solutions to develop the external calibration model.

The calibration protocol can include determining a relation between scavenging capacity and a parameter based on multiple standard solutions that contain no contaminated water involved in the AOP operation. the calibration protocol can include preparing multiple standard solutions comprising water and a standard scavenger compound at different concentrations; determining respective hydroxyl radical scavenging capacities of the standard solutions; adding to each standard solution an indicator; subjecting each standard solution to an oxidation process, to generate hydroxyl radicals that react with the indicator and the standard scavenger compound to partially degrade the indicator such that the resulting treated standard solution has a corresponding residual indicator content; and determining a residual indicator content parameter of each treated standard solution, to thereby obtain a relation between hydroxyl radical scavenging capacity and the residual indicator content to provide the external calibration model.

The monitoring protocol can include adding an indicator to the sample that is the same as added to the standard solutions; subjecting the sample to an oxidation process that is the same as added to the standard solutions, to generate hydroxyl radicals that react with contaminants and the indicator in the sample, to produce a treated sample; determining a residual indicator content parameter of the treated sample; and converting the residual indicator content parameter to hydroxyl radical scavenging capacity via the external calibration model and thereby determining the hydroxyl radical scavenging capacity of the water sample. The monitoring protocol can further include determining an interference value of the water sample prior to the oxidation process; and determining the residual indicator content parameter by factoring in the interference value. The interference value can be absorbance at the signature wavelength of the dye, and can be determined by obtaining an initial absorbance measurement of the water sample prior to the oxidation. The external calibration model can include a relation between scavenging capacity and $1/\Delta_{ln(absorbance)}$ wherein $\Delta_{ln(absorbance)}$ is the different between (i) natural logarithm of the initial absorbance measurement of the water sample prior to the oxidation process and (ii) the natural logarithm of the absorbance measurement of the treated sample after the oxidation process. The external calibration model can include a linear relation of scavenging capacity versus $1/\Delta_{ln(absorbance)}$. The external calibration model can include a relation between scavenging capacity and a difference between the initial absorbance measurement of the water sample prior to the oxidation process and the absorbance measurement of the treated sample after the oxidation process.

It is also noted in the context of the above methods and systems that the standard scavenging compound can include an alcohol, an alkene, or a ketone. For example, the standard scavenging compound can include trichloroethylene, ethylene, glyoxal, acetaldehyde, formaldehyde, diacetyl, 2-pentanone, acetone, camphor, sucralose, glucose, caffeine, dimethoxymethane, nitrobenzene, humic acids, or fulvic acids. Optionally, the standard scavenging compound comprises a secondary alcohol or a tertiary alcohol.

It is also noted that the external calibration model can include a curve of $1/\Delta_{ln(dye\ content\ parameter)}$ versus scavenging capacity, $1/\Delta$dye content parameter versus scavenging capacity, $\Delta$dye content parameter versus scavenging capacity, or dye content parameter versus scavenging capacity.

Various processes, methods, and systems are described and claimed herein for developing an external calibration model and for using determined scavenging capacity information in AOP operations. It is also noted that the features mentioned above can be combined together in various combinations.

DETAILED DESCRIPTION

Figure 1:
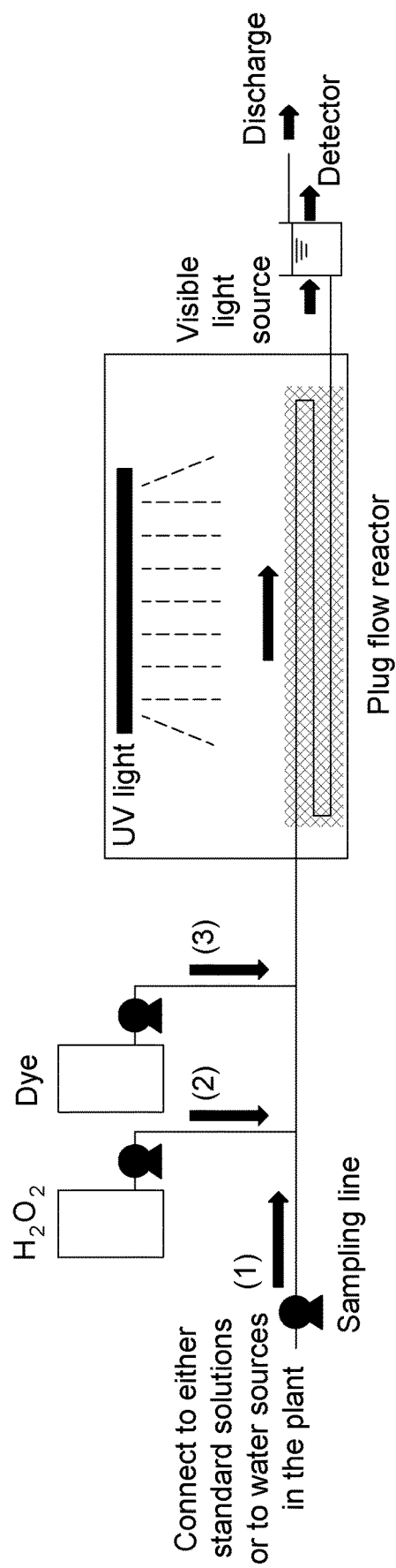
FIG. 1 is a side view schematic of an example test system that can be used to build an external calibration model for hydroxyl radical scavenging capacity and to monitor hydroxyl radical scavenging capacity of a contaminated water stream.

Using an external calibration model for determining radical scavenging capacity of contaminated water can be leveraged for enhanced operation of AOP operations.

The external calibration model can be prepared using standard solutions rather than samples of the contaminated water. The scavenging capacities of the standard solutions are determined, and then the standard solutions are subjected to a test oxidation treatment, which can involve the addition of an oxidant (e.g., hydrogen peroxide), a dye (e.g., methylene blue), followed preferably by an ultraviolet (UV) treatment to form hydroxyl radicals that are scavenged by species in the standard solution to form a treated solution. In some implementations, the residual dye content is then measured for the various treated solutions, preferably by determining absorbance at the signature wavelength of the dye. The absorbance data and the scavenging capacity data for the standard solutions can then be used to build the external calibration model, for example by plotting a scavenging capacity versus absorbance curve. In some alternative implementations, the oxidation treatment is performed to achieve a target dye degradation level (e.g., 20% degradation) and the reaction time to achieve that degradation level is determined and used to build the external calibration model, for example by plotting a scavenging capacity versus time (to achieve the target degradation) curve. While the description herein is mainly focused on the external calibration model based on scavenging capacity versus residual dye content (e.g., absorbance), it should be noted that the methods and systems described herein can be adapted for the alternative scavenging capacity versus time model, or other analogous models that could be developed.

Once the external calibration model has been developed, it can be implemented for determining the scavenging capacity of contaminated water. For example, a sample of the contaminated water can be obtained and then subjected to a substantially similar or identical treatment as the standard solutions, e.g., with the addition of an oxidant and a dye followed UV treatment at substantially the same dosages. The absorbance of the treated water sample is then obtained. The absorbance of the water sample can be identified on the external calibration model in order to determine the corresponding radical scavenging capacity of that water sample. If the external calibration model is based on scavenging capacity versus time to achieve a target degradation, then the time to achieve that degradation is determined for the water sample and the resulting time output is used to determine the corresponding radical scavenging capacity of that water sample.

The determined scavenging capacity of the water sample can then be used for control of an AOP operation that treats the contaminated water. For example, the determined scavenging capacity of the contaminated water can be used for feedforward control of oxidant and/or UV dosing. By knowing the scavenging capacity of the contaminated water to be treated by the AOP operation, the dosage of the oxidant and/or the UV dose can be provided efficiently for enhanced AOP performance.

It is noteworthy that the test oxidation system and its operating conditions used on the standard solutions to develop the external calibration model can be substantially the same as used on the contaminated water samples to determine scavenging capacity. The same oxidation process is thus conducted on the standard solutions and the contaminated water samples, and can involve hydrogen peroxide and UV treatment or vacuum UV treatment for example. These two oxidation processes can be preferred since they are more easily controlled compared to UV/ozone in which the dose of gaseous ozone can be more difficult to control, and compared to UV/TiO$_2$ in which particles can tend to interfere with the absorbance measurement. However, the AOP used to treat the main contaminated water stream can be any type of AOP that generates hydroxyl radials, e.g., hydrogen peroxide and UV treatments, UV/ozone treatments, UV/TiO$_2$ based methods, vacuum UV treatments, and so on, no matter which oxidation process the test system is based on.

Thus, while the oxidations processes used in the test system for calibration and monitoring should be the same, the commercial scale AOP that is operated based on the determined scavenging capacity can be different or the same as the test system.

Figure 7:
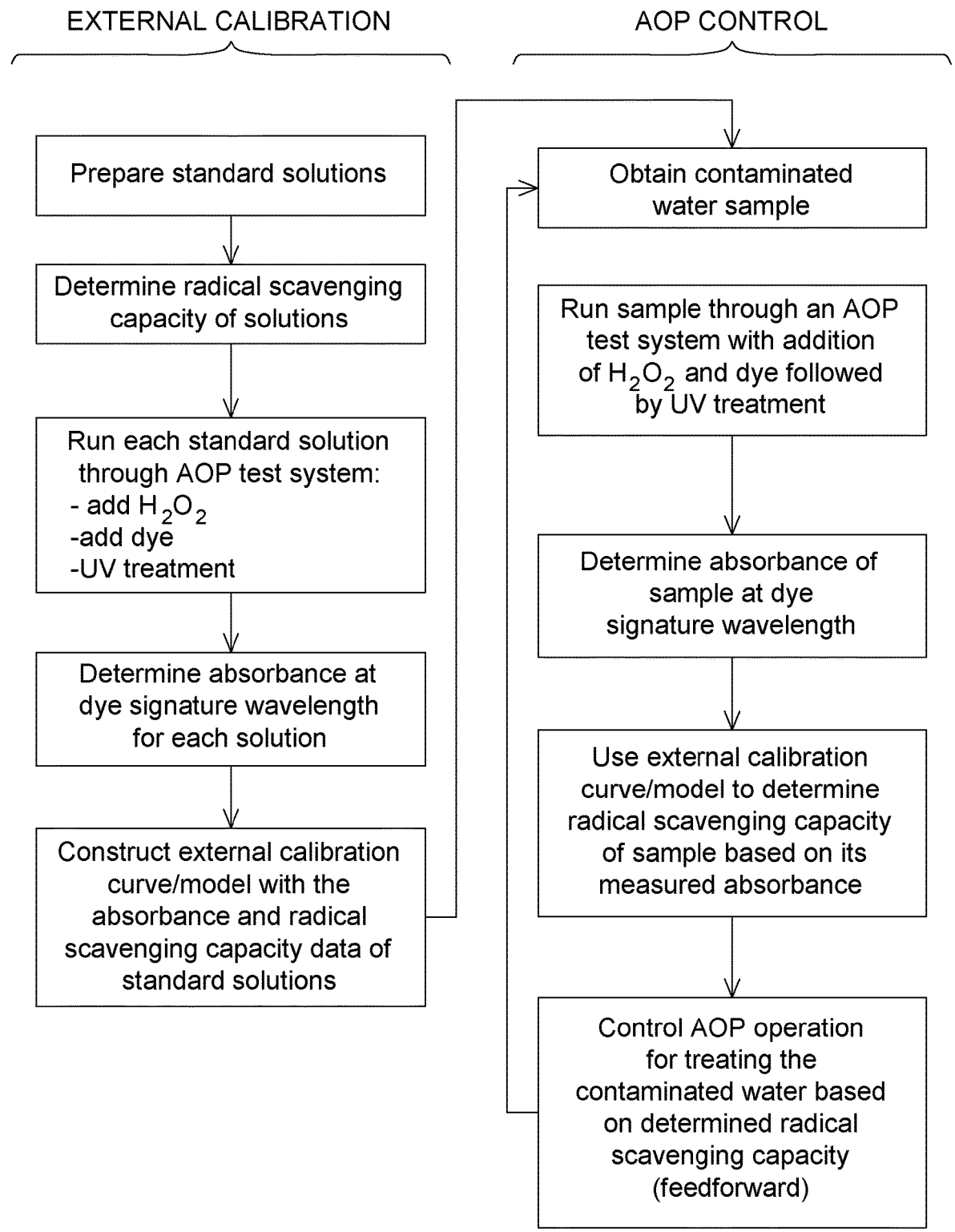
FIG. 7 is a process block diagram illustrating the development of an external calibration model for radical scavenging capacity and the use of the external calibration model for controlling an AOP operation.

FIG. 7 provides a block diagram illustration of a general example of the process of developing an external calibration model of scavenging capacity and then using the external calibration model for AOP control.

More details regarding the preparation of the external calibration model and its use in determining radical scavenging capacity and AOP control will be discussed below.

Preparing Standard Solutions

In some implementations, the standard solutions are not obtained from the contaminated water to be treated in the AOP operation. The standard solutions can thus be said to be "external" to the contaminated water.

The standard solutions can be prepared such that their radical scavenging capacities can be accurately determined and they can be processed in the test oxidation system to obtain data regarding residual dye content. The standard solutions are preferably selected and prepared with certain criteria in mind. First, the standard solutions can be prepared so as to have a stable scavenging capacity over a range of conditions, such as a range of pH values. For example, standard solutions having a composition that has a stable scavenging capacity over a wide range of pH (e.g., 4.5 to 9.0), can facilitate preparation of the standard solutions. Second, the standard solutions can be prepared to have good water solubility properties. Third, the standard solutions can be prepared to have low volatility to prevent evaporation. Fourth, the standard solutions preferably have no or low interference on the absorbance measurement (or alternative measurement that may be used) at the signature wavelength of the dye. Fifth, the standard solutions preferably have moderate reactivity with OH radicals (e.g., the rate constant can be in the range of about $2 \times 10^8$ to about $2 \times 10^9$ $M^{-1}s^{-1}$), since too high reactivity with OH radical can result in too much degradation of the standards at the desired test conditions, which could compromise the accuracy of the calibration curve; while too low reactivity can result in too high of a concentration of the compound to reach the desired scavenging capacity. Sixth, the standard solutions preferably have negligible direct reactivity with the UV light or the oxidizing agent (e.g., $H_2O_2$).

In some implementations, the standard solution comprises water and a standard scavenger compound. The standard scavenger compound can be an alcohol, for example. The alcohol can be selected to have low volatility, high water solubility, and high stability in terms of radical scavenging capacity. The high radical scavenging capacity stability can result from other properties, such as relatively high pKa value that inhibits losing or gaining protons. The stability criterion can also be considered in the context of the AOP treatment conditions to be used. Two example alcohols that can be used are isopropyl alcohol (IPA) and tert butyl alcohol (TBA), although various other alcohol compounds could be used. Other types of standard scavenger compounds that could be used with appropriate adjustments (e.g., lower concentrations compared to alcohols) and handling methods include certain alkenes (e.g., trichloroethylene, ethylene), certain aldehydes (e.g., glyoxal, acetaldehyde, formaldehyde), or certain ketones (e.g., diacetyl, 2-pentanone, acetone, camphor), or other compounds such as sucralose, glucose, caffeine, dimethoxymethane, nitrobenzene, humic acids, fulvic acids, and a mixture of two or more thereof.

One preferred example alcohol that can be used and has been tested is isopropyl alcohol (IPA). The rate constant between IPA and the OH radical is well documented as $1.9 \times 10^9$ $M^{-1}s^{-1}$; thus, if the concentration of the IPA is known, its scavenging capacity can be easily determined as the product of the rate constant and the IPA concentration. For example, 40 µM IPA solution has a scavenging capacity of $(40 \times 10^6$ M$) \times (1.9 \times 10^9$ $M^{-1}s^{-1}) = 7.6 \times 10^4$ $s^{-1}$. As IPA remains its molecular form within a wide range of pH without losing or adding protons (due to its relatively high pKa value), its rate constant with OH radical does not change within the normal pH range in water treatment. When the standard solution is prepared, there can be high confidence in its scavenging capacity without considering pH effect. In this sense, many organic acids may not be preferred as the standard solutions because their scavenging capacity is much more vulnerable to pH effect, and there would have to be a pH correction or control for such standard solution compositions.

Alcohols, such as IPA, also tend to be very soluble in water. The standard scavenging compounds can thus be selected based on its solubility in water. Other organic compounds, such as alkenes, aldehydes, ketones, and the like with relatively lower water solubility or higher volatility may not be as preferred in this sense. It should be noted, however, that other compounds could be used with appropriate adjustments to the test system and its operating conditions (e.g., lower concentrations) and handling methods of the standard solutions (e.g., depending on volatility). Some example compounds that can be used are mentioned further above.

The standard scavenger compound is present in the standard solutions at different concentrations, preferably covering a range of scavenging capacity sufficiently wide to be indicative of most contaminated waters that would be treated using AOP. For instance, the different concentrations can be provided in a range to cover most surface waters and/or scavenging capacity values encountered in drinking water treatment. However, it should be noted that the concentration range can be narrowed or broadened depending on the specific water matrix to be treated using AOP. In one implementation, the standard solutions are prepared such that the standard scavenger compound (e.g., IPA) is present from 0 to 120 µM. Within this range, the different concentrations can be every 2 µM, 5 µM, 10 µM or 20 µM, for example, with identical or different increments over the range.

The water in the standard solutions can be high purity water, such as Milli-Q® water. The composition of the standard solution is principally IPA in water and the scavenging capacity can be calculated as mentioned above. However, as the standard solution is exposed to the air, carbon dioxide can also become dissolved in the water, which makes the standard solution contain components other than IPA. The bicarbonate ($HCO_3^-$) formed after carbon dioxide is dissolved in the water will contribute to the overall scavenging capacity in a minor way as the rate constant between OH radical and $HCO_3^-$ is only $8.5 \times 10^6$ $M^{-1}s^{-1}$, much lower than that between OH radical and IPA which is $1.9 \times 10^9$ $M^{-1}s^{-1}$. To enhance the accuracy of the determined scavenging capacity of the standard solutions, the concentration of $HCO_3^+$ in the standard solution can be measured and the overall scavenging capacity of the standard solution can be modified by adding scavenging capacity of the bicarbonate to the scavenging capacity of the IPA.

In one implementation, the standard solutions include a single species as the standard scavenger compound, e.g., IPA or another alcohol as the sole standard scavenging compound besides $HCO_3^-$ ions. Alternatively, two or more different compounds could be used for each standard solution (e.g., IPA and TBA, humic acids and fulvic acids), in which case the pre-determination of the scavenging capacity would involve additional calculations. While single-component standard solutions are preferred, multi-component standard solutions are also possible.

The scavenging capacities of the standard solution at different concentrations of standard scavenger compound are determined by determining, for each standard solution concentration, the scavenging capacity of the standard scavenger compound and the scavenging capacity of one or more additional components (e.g., dissolved components, such as dissolved carbon dioxide in the form of bicarbonate ions), and then adding the scavenging capacities together to obtain an overall scavenging capacity for that standard solution concentration.

The scavenging capacity of each standard solution can be determined in various ways prior to subjecting the standard solution to the test AOP system. One method for pre-determining scavenging capacity is by calculation using the rate constant data from literature coupled with the concentrations of the standards, an example of which is mentioned above with respect to IPA. Another method for pre-determining scavenging capacity is using measurement techniques, e.g., method A described further below. It is also possible to use a combination of calculation and measurement techniques.

Test Oxidation System for Standard Solutions

Once each standard solution has been prepared, and has had its scavenging capacity determined, the standard solution is subjected to a test oxidation treatment, which uses an AOP technique to generate hydroxyl radicals.

FIG. 1 illustrates an example of the test system, which includes a sampling line and a sample supply pump; a hydrogen peroxide tank, a hydrogen peroxide addition line, and a hydrogen peroxide supply pump; a dye tank, a dye addition line, and a dye supply pump. A given standard solution is supplied through the sample supply pump and both hydrogen peroxide and dye are added to the standard solution at known quantities. The resulting sample mixture is then fed into a UV treatment unit where the sample mixture is subjected to UV treatment to produce a treated standard solution. Then, the treated standard solution is assessed for residual dye content, preferably by detecting absorbance at the signature wavelength of the dye.

While the illustrated test system in FIG. 1 is based on an $H_2O_2$/UV type AOP technique, it is noted that tests systems based on other types of AOP are also possible. It should be noted that the test oxidation system can be adapted in various ways for particular applications or particular AOP paradigms. For example, for some cases, the generation of the OH radical can be achieved with other processes such as UV/ozone and Fenton reactions, rather than with the UV/hydrogen peroxide process. In addition, a vacuum UV (VUV) oxidation process could be an advantageous alternative for the test system, as such processes could enable avoiding the requirement of primary oxidant additives, such as $H_2O_2$, in the test procedure and therefore facilitates simplification. VUV processes typically use very low wavelength light (e.g., 185 nm) into water and the light generates OH radicals from the water itself. Thus, the test oxidation system and used different routes and mechanism to generate the OH radicals in a repeatable and reliable manner. Preferably, the test oxidation system employs a single OH radical generation technique.

Furthermore, various dye compounds can be used in the context of the tests oxidation system. Alternatively, other types of indicator compounds could be used. Dyes can be particularly advantageous as they can be efficiently and effectively detected using absorbance techniques, which are simple, reliable, and cost-effective. However, it is possible to use other techniques to determine the residual dye content of the treated solutions. The dye can be methylene blue (MB) or various other dye compounds. In alternative implementations, another type of indicator can be used and the detection method can be adapted accordingly. For example, nitrobenzene could be used as an indicator and its residual content in the treated solution could be detected using methods other than absorbance. For real-time monitoring applications, it is preferred to employ a dye and absorbance measurements. However, for applications with intermittent measurement of the scavenging capacity, then compounds other than dyes could be used.

Figure 2:
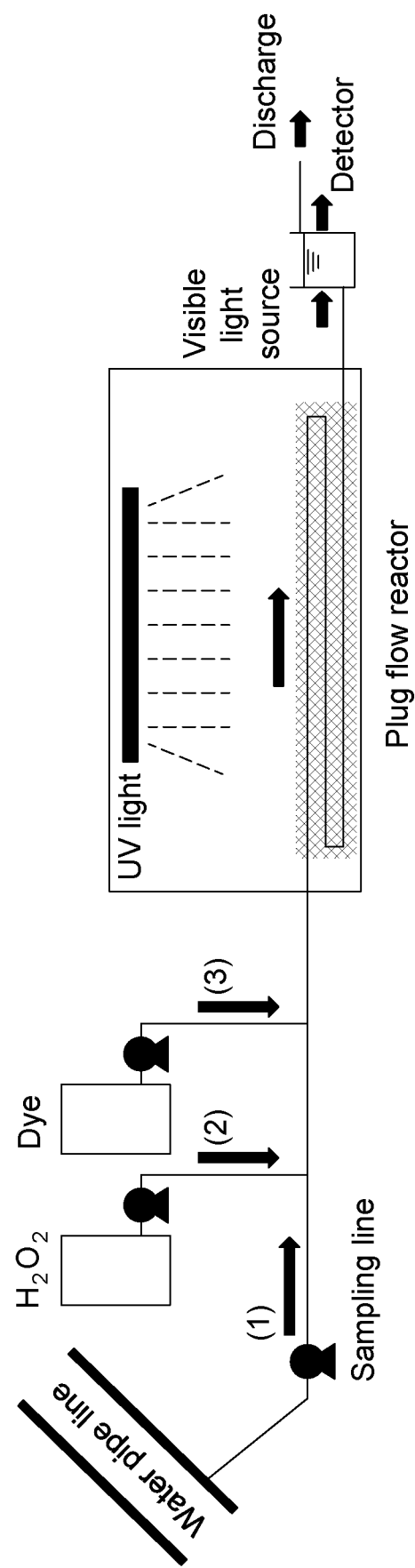
FIG. 2 is a side view schematic of a test system used to monitor radical scavenging capacity of a contaminated water slipstream withdrawn from a main stream flowing through a pipeline.
Figure 3:
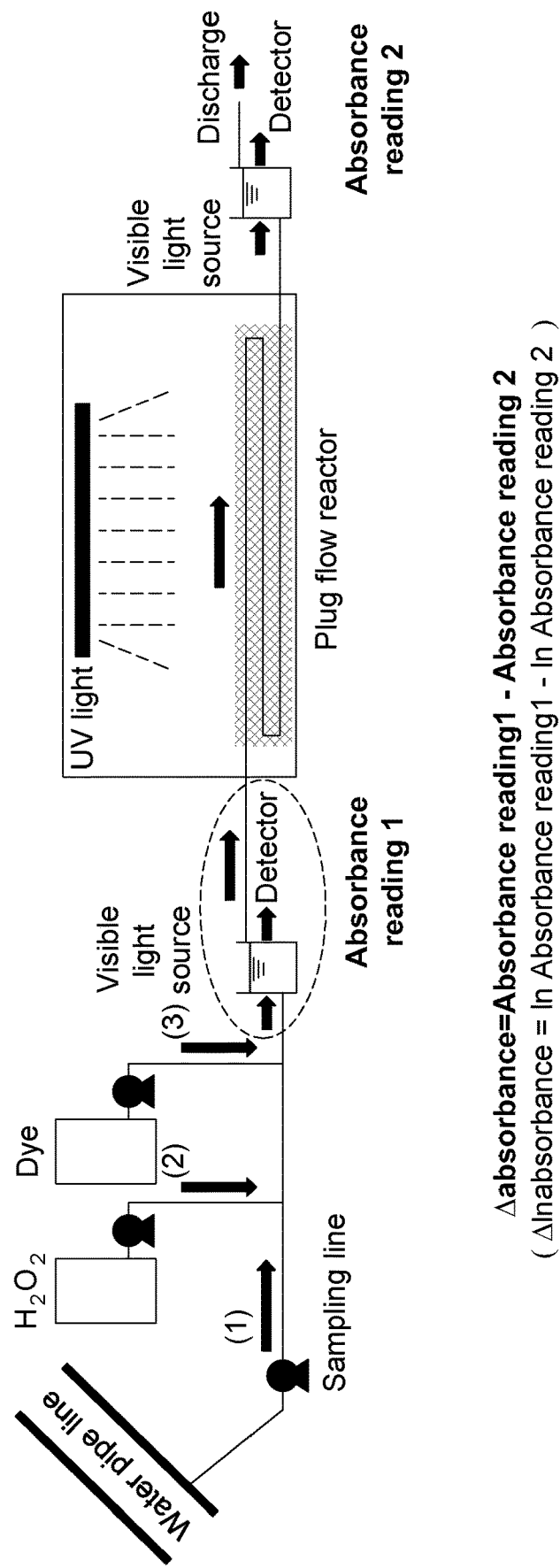
FIG. 3 is a side view schematic of another example test system used to monitor radical scavenging capacity of a contaminated water slipstream withdrawn from a main stream flowing through a pipeline, in this case measuring the absorbance of the influent and the effluent of the reactor. This design can improve the accuracy of the measurement and make the system applicable to a wide range of water samples.

Referring to FIGS. 1 to 3, it should be noted that the arrangement, configuration, and structure of the tests system can be different than the illustrated examples. For example, the layout of the different components of the system can be different, and the construction of each component can also be different. For example, the plug flow UV reactor can be a cuboid or a cylinder, horizontal or vertical; the UV lamp can be submerged in or over top of the water surface. Plug flow of the solution may be preferred, but a batch reactor can also be implemented. In addition, depending on the particular AOP paradigm that is being used in the test oxidation system, the particular components, steps, instruments, interconnections, and operating parameters can be modified.

Referring to FIG. 1, the standard solutions with different concentrations of the standard scavenger compound (e.g., IPA) are fed through the test system one by one, and the data regarding residual dye content (e.g., absorbance) is collected for construction of the external scavenging capacity model.

The dosages of the standard scavenger compound, the indicator/dye, and the OH radicals generated in the test system (e.g., via a certain UV intensity) should be selected in a balanced manner to facilitate obtaining accurate data. In addition, the selection of the UV intensity, oxidant (e.g., $H_2O_2$) dose, dye dose, and standard solution concentrations are water specific, which means that these values can vary from system to system depending on the water matrices that will be monitored and treated. Thus, for each water matrix to be monitored, a corresponding review of appropriate and preferred dosages, concentrations and intensities can be conducted. Nevertheless, there are some general principles to guide selection of reasonable values for these parameters.

First, as mentioned above, the standard solutions should be prepared so that the standard scavenger compound concentrations are representative of the scavenger concentrations in water samples that will be monitored. In other terms, the concentrations of the standard scavenger compounds should be broad enough to cover the possible scavenging capacity of the targeted water. For example, in the context of drinking water treatment, if IPA is used as the standard scavenger, the range of IPA concentrations could be from 0 μM to 120 μM, covering the range of the typical scavenging capacity of the water based on the scientific literature (i.e., $0-2.3 \times 10^5$ s$^{-1}$).

Second, the concentration of the dye should be selected to be high enough to be accurately detected spectrometrically, and high enough to be a dominant absorber of UV photons, together with the $H_2O_2$ (i.e., MB and/or $H_2O_2$ should absorb far more photons than other constituents in the water when UV/$H_2O_2$ oxidation is used). On the other hand, the concentration of the dye should preferably not be so high as to exceed the applicable range for the Beer-Lambert law (i.e., the absorbance of the MB should remain linearly proportional to its concentration); otherwise, a linear calibration curve would be hard to establish. For example, if MB is used as the indicator in the scavenging capacity monitoring system, its concentration is recommended to be in the range of about 1 μM to about 10 μM, preferably about 4 μM to about 8 μM. Note that in practice, the MB concentration can be fixed while the IPA concentration may vary depending on the scavenging capacity of the water being tested.

Third, the concentration of $H_2O_2$ can be in the range of 5-50 mg/L, and high values are preferred because, in combination with the applied dye, they should absorb the majority (e.g., at least 90%, at least 95%, at least 98% or at least 99%) of the UV photons. When another oxidant is used, its concentration can be modified accordingly based on similar principles.

Fourth, the UV intensity should preferably be able to generate enough OH radicals to degrade approximately 20% of the dye in a reasonable time (e.g., time from a few seconds to several minutes can be considered as reasonable). UV intensity that is too weak can lead to too long a reaction time to achieve such dye degradation levels, which will make the online monitoring undesirably slow (e.g., no longer "real-time"). If a low UV intensity is used along with a short reaction time, then there can be insufficient degradation of the dye to provide meaningful and accurate output data. In other words, the "AOP dose" (e.g., resulting from UV intensity and $H_2O_2$ concentration) should be high enough to result in sufficient reactions with and degradation of the dye over the different standard solution concentrations so that the absorbance measurements of the residual dye provide enough differentiation for the calibration model.

In addition, the standard scavenger compound and the dye concentrations should be provided in coordination with the AOP dose (i.e., amount of OH radicals that are generated) so that they do not significantly degrade during the treatment. Only a small amount of the scavengers and the dye in the samples should be destroyed. For instance, if the AOP dose is too high and/or the concentrations of scavenger and dye are too low, then the absorbance measurement can become inaccurate. The treated solution exiting the UV treatment cell should have a relatively similar scavenging capacity and scavenger concentration compared to the original standard solution, and thus the degradation of the scavenger is relatively low. Therefore, at the end of the test, the scavenging capacity of the samples (including the standard solutions and the real contaminated water samples) should not change much. For example, if MB is used as the indicator, the degradation of the MB is ideally to be less than about 20%, 15% or 10%.

Furthermore, dye and hydrogen peroxide concentrations should be high enough to overshadow water matrix effects, and thus can depend on water composition. With such concentrations of dye and hydrogen peroxide being "spiked", the UV-absorbing properties of all of the influent will be almost the same. This is an advantageous aspect as it validates the externally-calibrated system and facilitates its application to different contaminated water samples. The amounts of hydrogen peroxide and dye added to the standard solutions are preferably provided such that there is sufficient dye to have residual dye content. The hydrogen peroxide and dye can thus be added in relatively high concentrations to overshadow any matrix effects because the same concentrations will be applied later in real water samples. Again, these parameters are water-specific, such that if the contaminated water to be monitored has an inherent absorbance beyond some value, it may be preferred to increase the amount of hydrogen peroxide and/or dye being used in the test system or to dilute the contaminated water.

By way of example, the following ranges and values for dye concentration, hydrogen peroxide concentration, standard scavenger compound concentration, and UV intensity are provided:

In drinking water treatment, hydrogen peroxide can be provided in a concentration of 10 to 50 mg/L and the dye can be provided in a concentration of 1 to 10 μM, for example. The average UV intensity at the water surface can be between (100-1000 μW/cm$^2$). The standard scavenger IPA can be provided from 0 to 120 μM to develop the external calibration model. Ratio of dye to standard scavenger at its upper concentration can be between about 1/120 to about 1/12.

In other water treatment applications, hydrogen peroxide can be provided in a concentration of 5 to 500 mg/L and the dye can be provided in a concentration of 1 to 20 μM. The UV intensity can be between 50 to 5000 μW/cm$^2$. The standard scavenger (e.g., IPA) can be provided from 1 to 500 μM to develop the external calibration model. Ratio of dye to standard scavenger at its upper concentration can be between about 1/500 to about 1/25.

In some implementations, the degradation percentage of the dye in the test system is between about 1% and about 40%, between about 2% and about 35%, between about 3% and about 30%, between about 4% and about 25%, or between about 5% and about 20%, for example. Various other sub-ranges in between these values could also be implemented. In some preferred embodiments, the dye degradation percentage is between 5% and 20%, meaning that around 5% is degraded when scavenging capacity is low and around 20% is degraded when the scavenging capacity is high, such that the degradation range between upper and lower scavenging capacities to be tested is about 15% (i.e., 20% minus 5% in this case). The degradation range can be between 5% and 30%, for example. Furthermore, the maximum degradation percentage of the dye can be approximately 50%, 40%, 35%, 30%, 25%, 20%, or 15% with ±5%. The degradation characteristics of the dye in the process can be provided according to the accuracy requirements of the monitoring system, depending on the tolerance of the test error regarding the monitoring purpose.

It should be noted that when other oxidation processes are used for the test system, the operating conditions and corresponding dosages can be modified accordingly. Routine tests can be performed to determine the tolerances of the concentrations and dosages of the additives and UV treatment parameters, to provide a recommended operating envelope for the test oxidation system. The selected concentrations of the oxidant (e.g., hydrogen peroxide) and indicator (e.g., dye, such as MB) that are used in the test oxidation system can depend on various factors. For example, they can depend on the concentration range of the standard scavenger compound being used which can depend on the eventual industrial application of the external calibration model; on the chemical nature of the standard scavenger compound being used (e.g., IPA versus other alcohols or other compounds); on the particular oxidant and/or indicator that are used; among other factors.

Figure 8A:
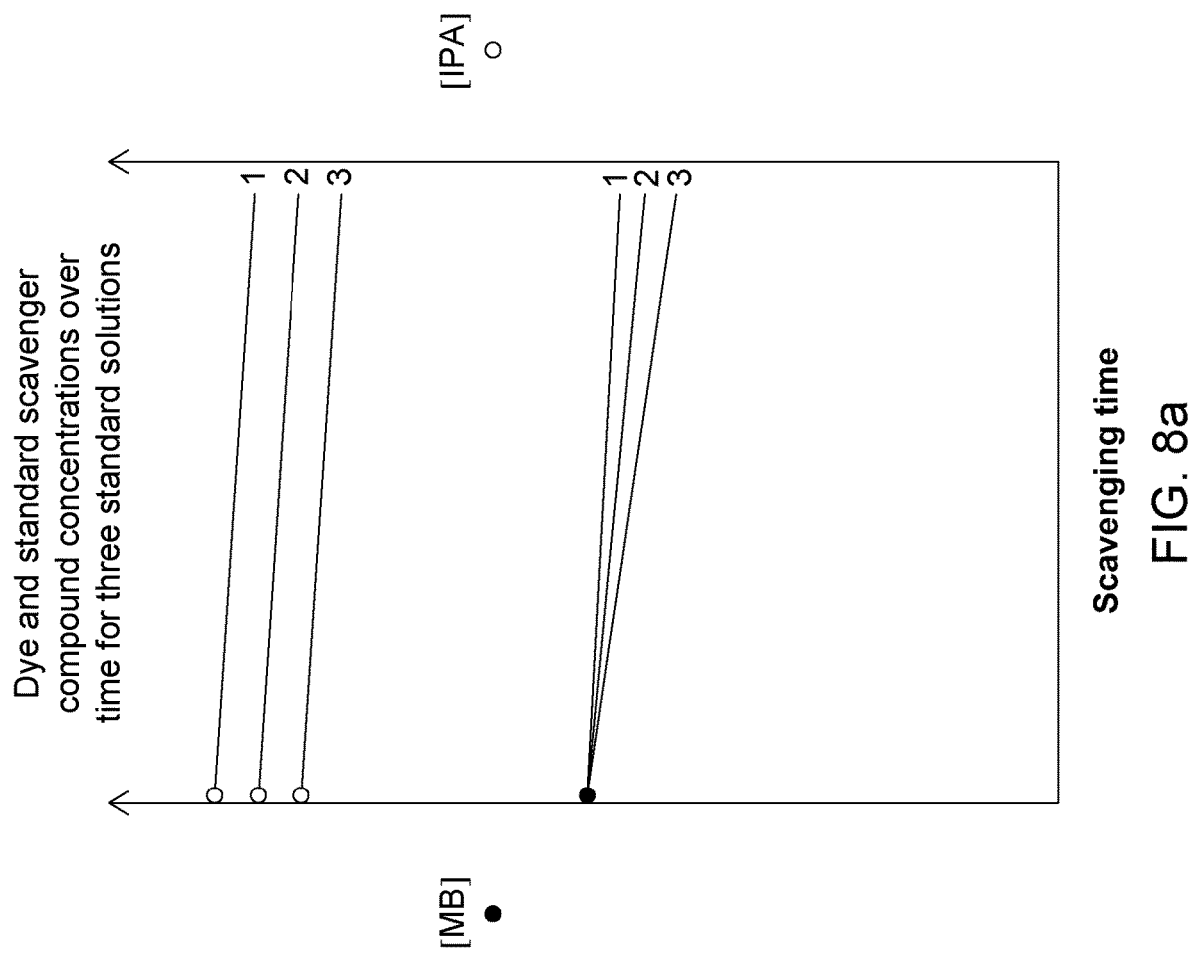
FIGS. 8a and 8b are conceptual graph of dye and standard scavenger compound (IPA) concentration versus time during oxidation reaction.
Figure 8B:
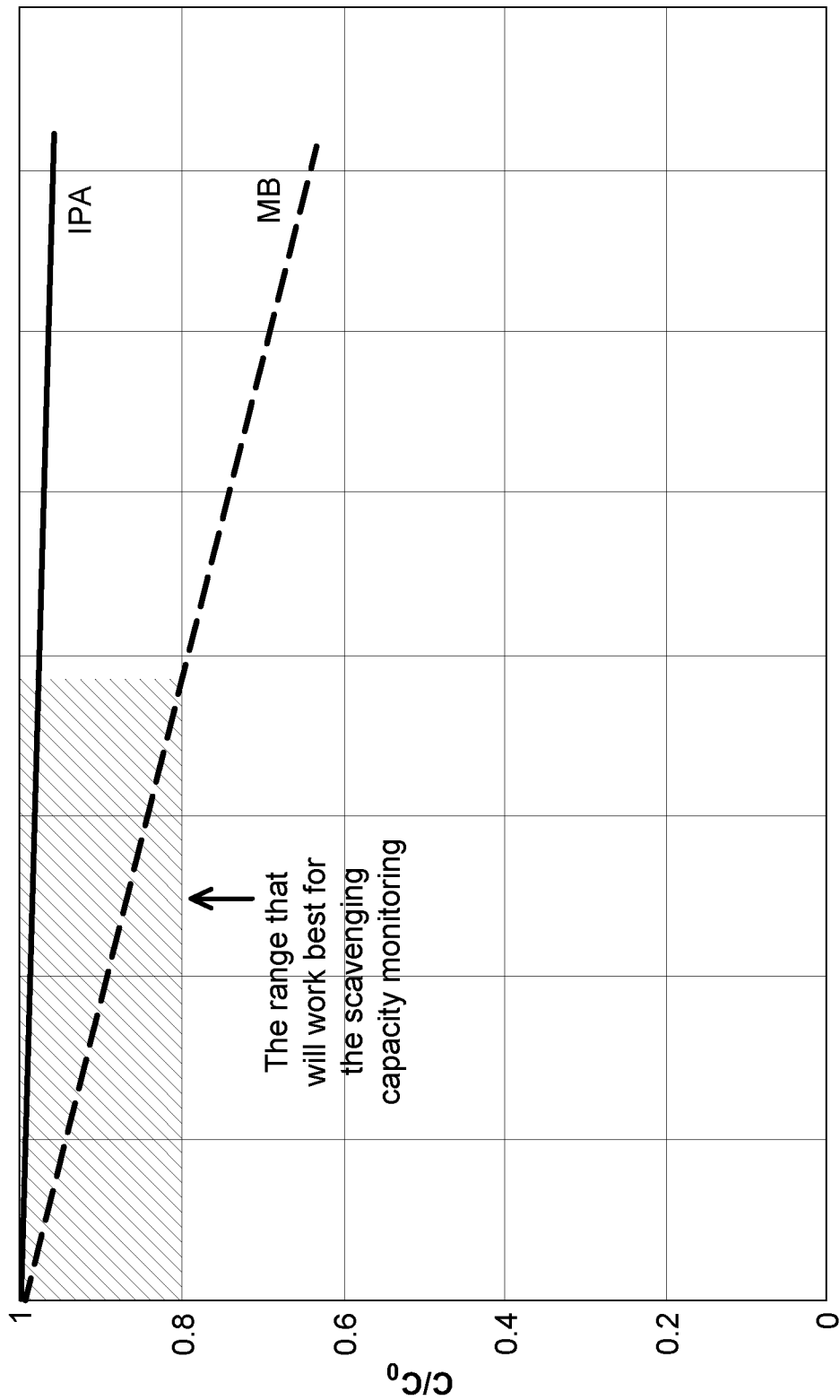

In this regard, FIGS. 8a and 8b provide useful visualization of the impact of hydroxyl radicals on the dye (e.g., MB) and the standard scavenger compound, illustrating the evolution of the concentration of these compounds over time during oxidation. It is noteworthy that the reaction rates involved in the degradation of the MB and standard scavenger compound are not particularly relevant. As shown in FIGS. 8a and 8b, both the dye and scavenger compound undergo some degradation over time due to reactions with hydroxyl radicals. The overall degradation of the standard scavenger(s) is not significant, as the residual concentrations are still relatively close to starting concentrations. As can be best seen in FIG. 8a, the initial concentration of the dye is the same for each run, while the initial concentration of the standard scavenger compound (e.g., IPA) changes for each run. Since at lower scavenger compound concentrations there is less IPA to react with the hydroxyl radicals, more dye reacts with the radicals and undergoes higher degradation yielding a lower residual concentration after oxidation.

FIG. 8b was constructed using a mathematical model to simulate the degradation of IPA and MB and thus can be considered to be accurate. From this figure, very limited IPA (about 2%) is degraded while about 20% MB degradation occurs. 20% MB degradation may be considered a "typical" target for the scavenging capacity test system. More MB degradation would require more time in the UV cell and would not improve accuracy. In addition, the products of IPA degradation may still contribute to the scavenging capacity, making the scavenging capacity of the IPA solution potentially approximately constant from the beginning to the end of the test.

Figure 10:
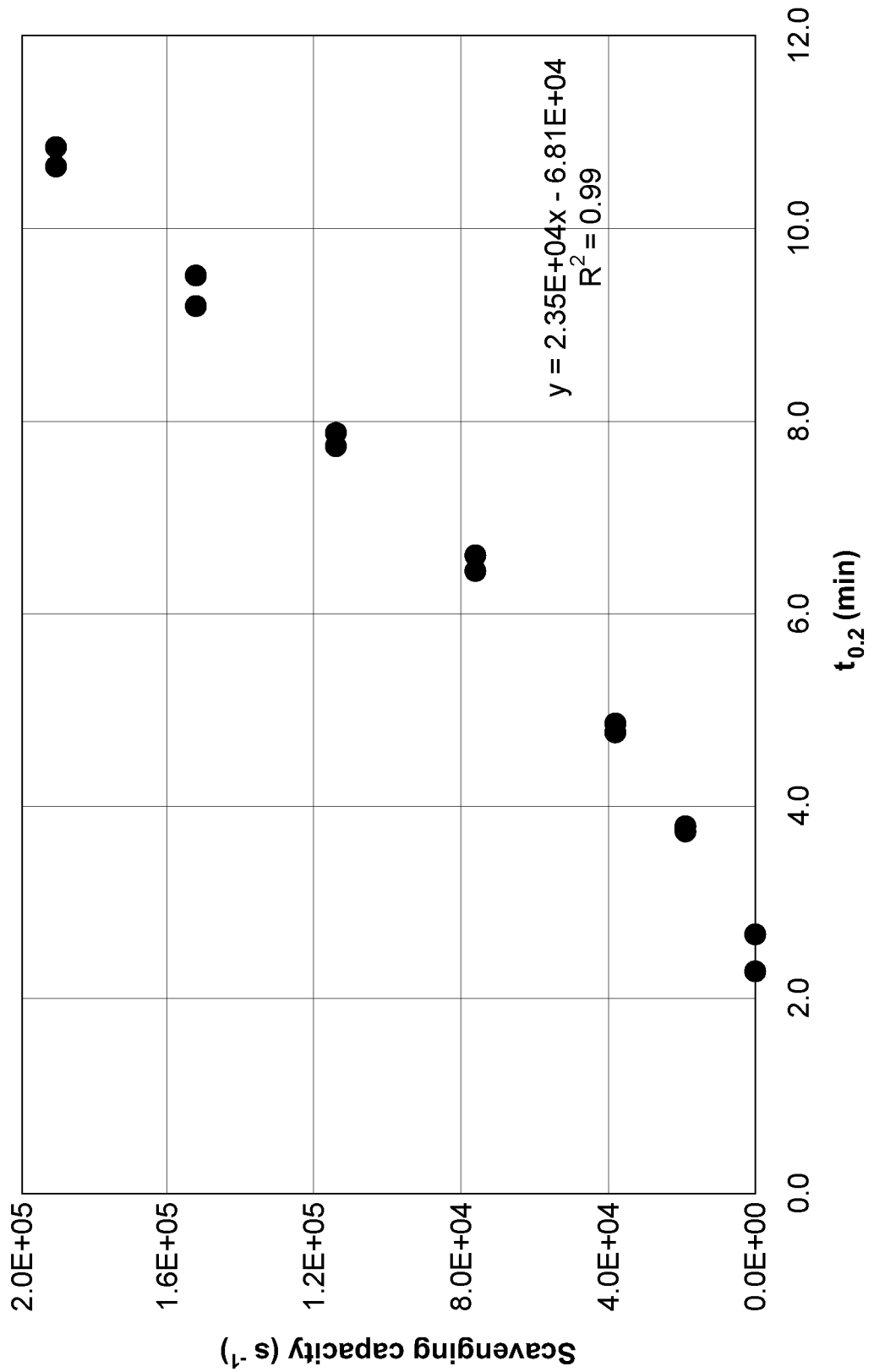
FIG. 10 is a graph of scavenging capacity versus reaction time to achieve a target dye degradation of 20%.

As mentioned further above, one implementation of the test system and its application involve a constant reaction time (i.e., in the UV cell) and establishing the external calibration model as "residual dye content (absorbance) variable vs scavenging capacity variable". In other words, for a water sample, MB decay is measured over a fixed reaction time and then the external calibration model is used to report the scavenging capacity in that water sample. The schematics of the system (e.g., FIGS. 1 to 3) implies that the reaction time is fixed, and governed by the selected flow rate of the sample through a fixed length of pipe in the UV cell or reactor. However, an alternative implementation is also possible, where a target dye degradation is held constant and time is the measured variable. In this alternative approach, one measures how much time it takes to degrade the dye to some fixed and convenient value, such as 20% for example. The higher the scavenging capacity, the longer the time it will take to achieve this fixed level of dye degradation. An example calibration curve using this method is shown in FIG. 10. In this alternative implementation, some of the system components and their operation would be modified compared to the absorbance-versus-scavenging capacity approach. For example, the online monitoring of the water samples would not be continuous, since the sample flow through the device would preferably be in batch mode. In the absorbance-versus-scavenging capacity configuration, the sample flow could run continuously through the pipe and across the UV reactor. Thus, for the alternative time-versus-scavenging capacity model, the plumbing and operation of the test system would be modified.

Construction of External Calibration Model

As noted above, there are several ways to develop the external calibration model, which may be based on "residual dye content versus scavenging capacity" or "time to achieve target dye degradation versus scavenging capacity", for example.

Figure 9:
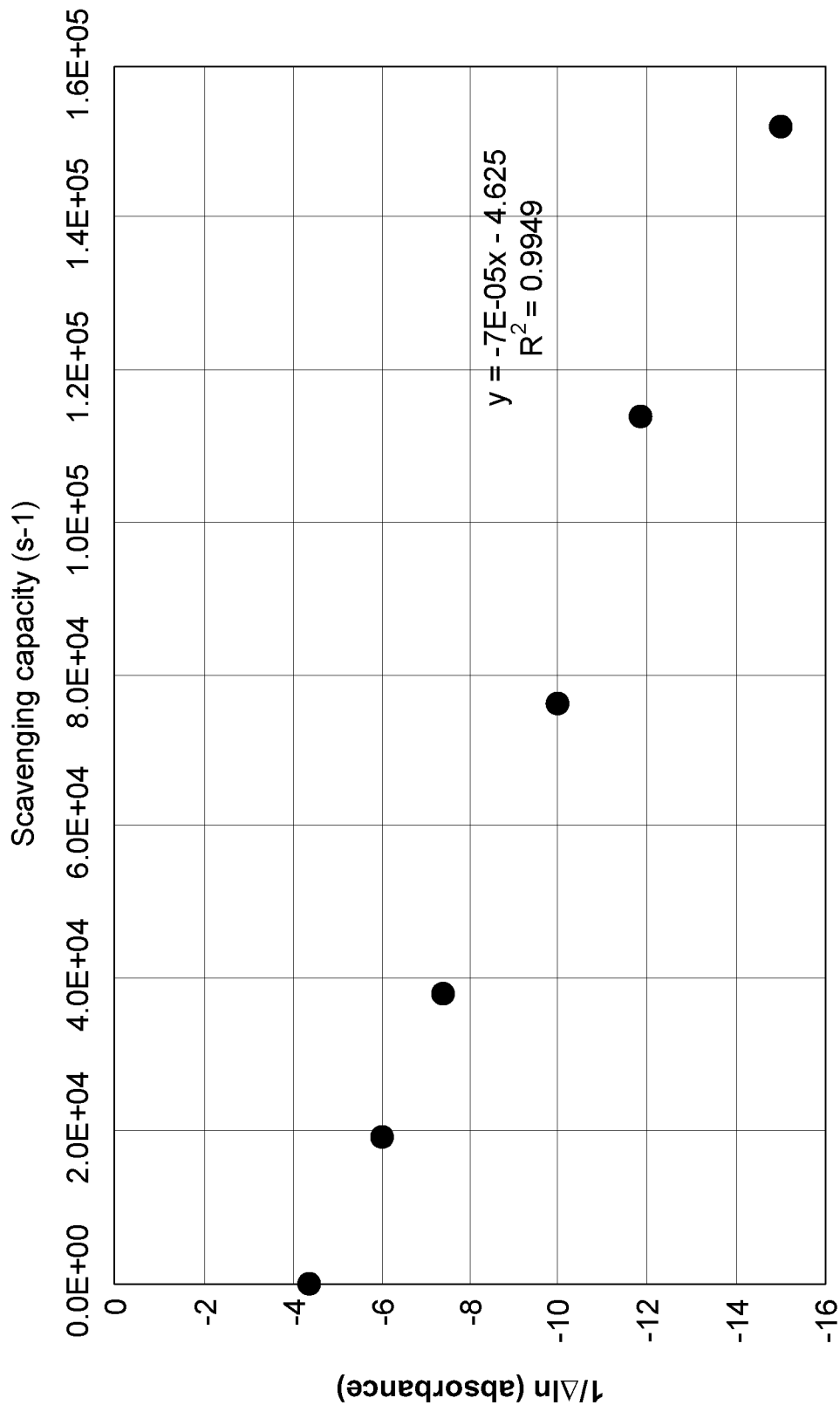
FIG. 9 is a graph of $1/\Delta_{ln(absorbance)}$ versus scavenging capacity, which provides an example of an external calibration model.

In some implementations, the treated standard solutions are preferably assessed for residual dye content by evaluating absorbance at the dye's signature wavelength to obtain absorbance data. In such cases, the external calibration model can include a calibration curve relating scavenging capacity to absorbance. FIG. 9 provides an example of such a curve of $1/\Delta_{ln(absorbance)}$ versus scavenging capacity, which gives a linear relation. Other plots of scavenging capacity versus an absorbance related variable (e.g., absorbance, $\Delta$absorbance, 1/absorbance) are also possible. In addition, it should be noted that the external calibration model can include other variables such that it includes the relation between scavenging capacity and a measurable variable related to or indicative of residual dye or indicator content.

The external calibration model can be stored on a computer or another physical medium for future use in the context of AOP operations. It can take the form of a scavenging capacity versus absorbance graph, for example. As the standard solutions used to prepare the external calibration model are typically provided at certain increments over a certain range of the scavenger compound (e.g., every 20 μM from 0 to 120 μM), the external calibration model can be constructed to extrapolate between values and/or beyond high- or low-end values using various extrapolation methods (e.g., linear or polynomial based extrapolation techniques, regression analyses, and so on). However, as noted above, it may be preferred to use a range of standard scavenger compound concentrations that represents the range of scavenging capacities that will be encountered in the industrial application, and thus extrapolation beyond the end points of the curve may not be necessary.

The external calibration model can be determined once or updated several times during the course of using it in AOP operations. Regular updating of the calibration model by periodically running through a series of standard solutions is preferred. If the test system is manufactured in the same way (e.g., the same configuration, the same materials, and the same lamp) as the calibration system and its operating parameters and properties can be maintained over time, then the calibration can be "universal" and independent of the drinking water treatment facility. In other words, an external calibration model that is developed using a certain test system design can be used for process control in an AOP plant if the test system that is implemented in the AOP has a substantially similar and preferably identical design and operation as the test system used for calibration. Developing a universal calibration curve can be facilitated by having a configuration of the test system that can be consistently reproduced and can operate in a stable and consistent fashion over time. Test systems that use components with high consistency and reproducibility can be used for universal calibration situations, for example by using UV light from LEDs which can be more stable compared to traditional mercury arc discharge UV lamps. Alternatively, there could be a sensor arrangement in the test system that can independently and reliably track the light/reaction conditions to allow an operator to forego onsite calibration.

However, it can be advantageous to develop a calibration model using a particular test system to be used in the AOP plant, both at the beginning and periodically during operations. Regularly validating and updating the external calibration model is thus preferred over the universal calibration scenario. Fortunately, this calibration process can be easily standardized and conducted at industrial sites.

Developing the external calibration model has been found to successfully avoid the difficulties involved in calculating UV dose and OH radical generating rates, measuring the MB concentrations, and the cumbersome mathematical calculation processes that are involved in other methods. Still, it should be noted that the methods described herein can be further refined by using additional measurements, calculations, units, and steps, if desired.

In an alternative implementation, the external calibration model is based on the relation between scavenging capacity and time to achieve a target dye degradation. An example of this type of external calibration curve is shown in FIG. 10.

Use of External Calibration for AOP Control

Figure 6:
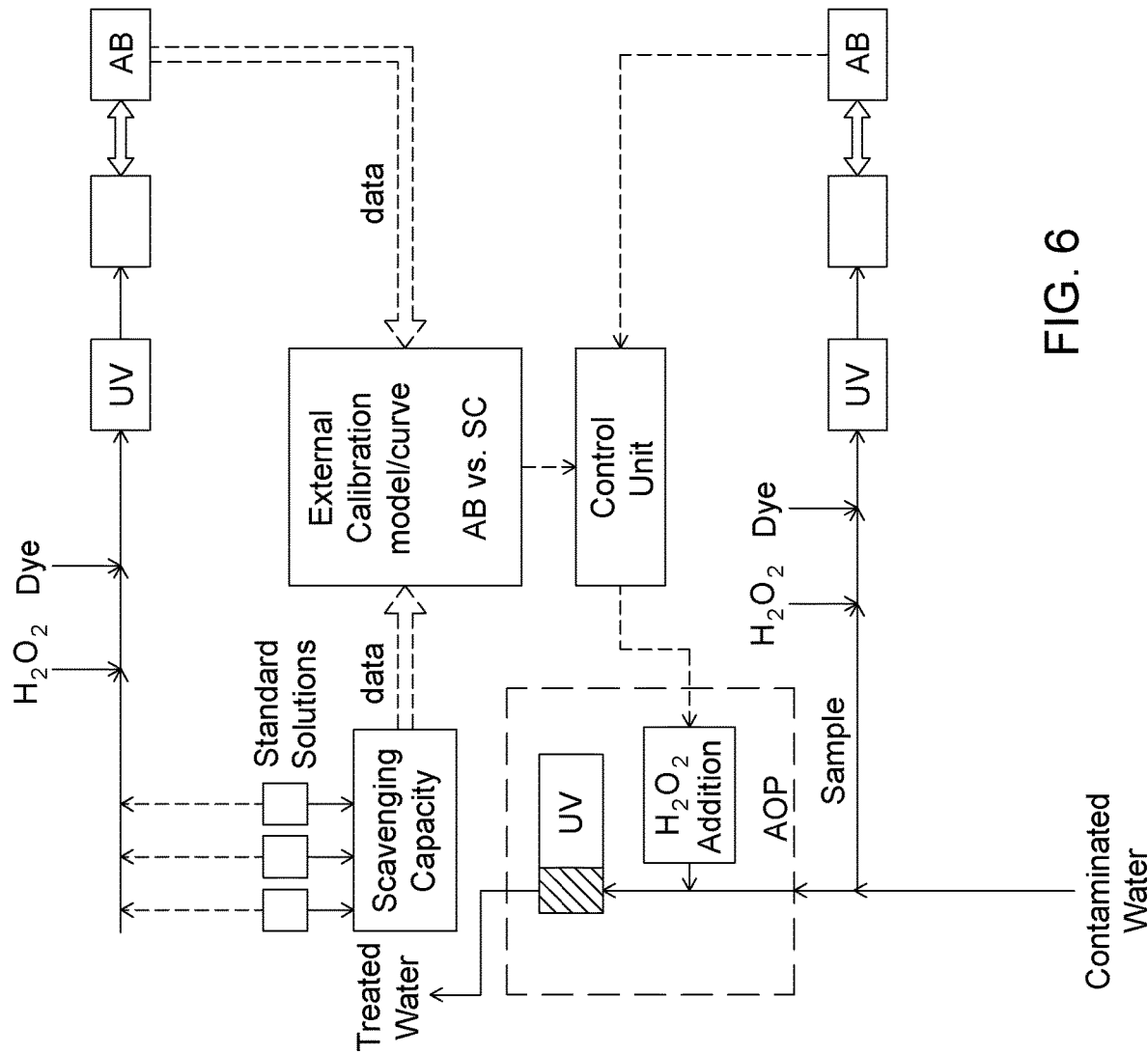
FIG. 6 is a block diagram illustrating test systems for building an external calibration model for radical scavenging capacity and then to monitor radical scavenging capacity of a contaminated water stream using the external calibration model.

Referring to FIGS. 2, 3 and FIG. 6, once the external calibration model has been developed it can be used in the context of controlling an AOP operation. In particular, a sample of contaminated water can be obtained from a main contaminated water stream upstream of the oxidation treatment, analyzed by running the sample through the test system to obtain an absorbance reading. The absorbance reading for the sample can be compared to the external calibration model in order to derive a radical scavenging capacity for that sample, which can then be used to adjust downstream AOP unit operations. This type of process control can be said to be feedforward as the contaminated water is sampled and tested, and then downstream unit operations are adjusted accordingly.

In some implementations, the sample is a slipstream that is withdrawn from the main stream of contaminated water. The slipstream line can be in fluid communication with the supply line of the AOP test system, as illustrated, or it can be fed into a holding tank to which the sample supply line is coupled. Alternatively, the sample can be obtained using other methods.

It should be noted that, in practice, the test system used to analyse the standard solutions and obtain the external calibration model can be used, after calibration, as the test system for analyzing the samples of contaminated water. Once the calibration has been done, the supply line can simply be connected to the appropriate tank or line in the AOP plant to receive real process samples of the contaminated water. By using the same system, enhanced consistency and therefore accuracy can be facilitated. Alternatively, the different test system can be used for the AOP plant compared to the system used for the calibration, although it is preferred that the two systems be as similar as possible in terms of dimensions, setup, and operating conditions. Using different systems can be useful if there is a single calibration system and then multiple control systems implemented in one or more AOP plants. If a system implemented in an AOP plant for process control is identical to the system used to generate the external calibration model, the determination of radical scavenging capacity and the process control should be robust and accurate.

Once the external calibration model has been developed, it can be used to provide real-time online monitoring and process control. FIG. 6 provides an overall view where a system is first used to develop the external calibration model, which is then used by a control unit that receives absorbance data regarding water samples and provides process control to the UV dose and/or the hydrogen peroxide addition unit, e.g., to adjust dosage according to the scavenging capacity of the incoming contaminated water stream.

It is also noted that one or more of these test systems can be installed in an AOP plant, at various points along a given process line and/or for monitoring different process streams in the plant. Depending on the given stream to be monitored and the given unit operation to be controlled, each test system can be calibrated and then operated accordingly. Preferably, a monitoring system can be installed upstream of primary oxidant addition and UV treatment, to facilitate feed-forward control based on determined scavenger capacity of the contaminated water stream to be treated. It is also noted that a monitoring system could be installed downstream of UV treatment such that scavenging capacity of the treated water can be assessed and, the AOP could be adjusted using feed-back control. Various combinations of control strategies can also be used, e.g., by installing multiple systems at different locations to monitor scavenging capacity of different process streams. In addition, in order to provide redundancy and robust operations, multiple monitoring systems can be installed to monitor scavenging capacity of a given process stream, in which case one of the systems can be taken off-line for re-calibration or maintenance while the other continues to provide monitoring data for process control.

A control unit or "controller" can be coupled to the monitoring system and the AOP unit operations to enable process control. The controller can receive and process data (e.g., absorbance measurements) from the monitoring system, and can determine the scavenging capacity based on the calibration model that can be stored in memory, and can also be coupled to one or more units of the AOP to control oxidant dosage and/or UV treatment parameters. The controller may be implemented in hardware or software, or a combination of both. It may be implemented on a programmable processing device, such as a microprocessor or microcontroller, Central Processing Unit (CPU), Digital Signal Processor (DSP), Field Programmable Gate Array (FPGA), general purpose processor, and the like. In some embodiments, the programmable processing device can be coupled to program memory, which stores instructions used to program the programmable processing device to execute the controller. The program memory can include non-transitory storage media, both volatile and non-volatile, including but not limited to, random access memory (RAM), dynamic random access memory (DRAM), static random access memory (SRAM), read-only memory (ROM), programmable read-only memory (PROM), erasable programmable read-only memory (EPROM), electrically erasable programmable read-only memory (EEPROM), flash memory, magnetic media, and optical media.

Additional Information Regarding Scavenging Capacity Determinations

Existing methods for determining radical scavenging capacity described by Rosenfeldt and Linden (2007) involve heavy mathematical deductions. These mathematical equations are valid only under ideal conditions, such as a constant OH radical concentration, zero change of the $H_2O_2$ concentration, pseudo-first order reaction, and that the dye concentration can be accurately quantified by absorbance measurement. In reality, such conditions rarely exist. In other words, many assumptions are made before such mathematical models can be used to measure scavenging capacity in an accurate and consistent fashion. Depending on how much the assumptions deviate from the reality, errors from 20% to 2000% can occur. The general idea behind the Rosenfeldt and Linden method is to measure the different degradation rates of a probe compound under UV exposure at different $H_2O_2$ concentrations in the water sample; then plot the degradation rate versus $H_2O_2$ concentrations. The scavenging capacity can be calculated from the slope and the intercept of the fitted line. See Rosenfeldt, E. J. and Linden, K. G. (2007) "The $R_{OH,UV}$ Concept to Characterize and the Model $UV/H_2O_2$ Process in Natural Waters". Environmental Science & Technology 41(7), 2548-2553, for further details. For one sample, the Rosenfeldt and Linden method typically takes hours to measure the scavenging capacity. In comparison, the method described herein can determine the scavenging capacity virtually instantaneously.

There are several differences between this conventional method (also referred to as "method A" herein, a method employed by Xylem Water Solutions Herford GmbH) and the test methods described herein using an external calibration model (an example of which is also referred to herein as "method C"). One difference is that method A requires a determination of the quantity of OH radical that is generated. This is why there is a UV intensity detector in method A. However, from the configuration of method A's device, it was found that there are various possibilities for errors in this method, e.g., a) the UV system is not a collimated beam system, and the light intensity can be difficult to be accurately determined; b) the configuration of the device used to measure the UV intensity is after it passes through the cell, whereas a better way of measuring the intensity is to measure it at the surface of the sample; c) the device requires the water depth and UV-adsorbing properties of the water to calculate how much OH radical is generated but these parameters are not necessarily mentioned in the method or readily available; d) even with the UV intensity and water UV absorbance correctly measured, many assumptions are still required to calculate the OH radical generating rate, which is likely to lead to more errors. For example, the concentrations of the dye have to be accurately calculated, which might be difficult as explained below; several correction factors such as reflection factor, divergence factor, Petri factor have to be applied and all have their own errors. It is noted that there are different reaction pathways between OH radical and dye (and other dyes), some resulting in de-coloration and some not. Therefore, de-coloration may not embody an accurate assessment or indication of dye degradation and/or the degradation of other dyes, which means method involving colorimetric "quantification" of dye concentration may have lower accuracies.

Another difference is that the method C does not require and preferably does not involve heavy mathematical calculation. The mathematical model that method A uses to calculate the scavenging capacity also involves the same assumptions as mentioned above, such as a constant OH radical concentration, zero change of the $H_2O_2$ concentration, pseudo-first order reaction, etc.; and these will add errors to the results. Examples of the methods described herein do not include such heavy calculations. In fact, in examples of methods described herein, the methods circumvent detailed modelling by building a "black box" type model, where the input is the dye degradation/dye residual content (e.g., via absorbance), while the output is the scavenging capacity. Once the black box model is calibrated, any dye degradation can be converted to a scavenging capacity value. By circumventing the complex mathematics, modelling, and assumptions, example methods disclosed herein can also avoid errors associated with such complex mathematical models.

It is also noted that different scavenging species react at different rates with OH radical. However, these reaction rate discrepancies are not important for the external calibration methods described herein. The calibration method relates to the overall scavenging capacity, which is a parameter of additive property. For example, the overall scavenging capacity is the sum of the scavenging capacity of each species. Compounds with low reaction rate but in high concentrations might have the same scavenging capacity compared to compounds with high reaction rate but in low concentrations. So, the parameter "scavenging capacity" itself does not differentiate between different species. Theoretically, the calibration curve can be established with any samples with known scavenging capacity, and this calibration curve will be universally applicable.

It is also noted that the AOP that is controlled using techniques described herein can be configured and operated to treat various streams and sources of water. For example, the AOP can be used to treat drinking water, tap water for industrial processing purposes (e.g., manufacturing microchips), waste water, leachate, or any other types of contaminated water, such as contaminated surface water (e.g., lakes and rivers) and groundwater. The AOP can be part of a primary, secondary or tertiary treatment process. The contaminated water can include one or more contaminants of various types, such as organics, aromatics, pesticides, volatile organic compounds, inorganic pollutants, biological pathogens, and so on.

It is also noted that commercialization of technology described herein can facilitate resolving or mitigating environmental impacts as well as conserving the natural environment and resources. For example, accurate and efficient scavenging capacity determination can be used to avoid overdosing or underdosing in the context of AOP plants, which can in turn facilitate producing cleaner water more efficiently.

EXPERIMENTATION

Various experiments have been conducted to assess methods and systems for determining hydroxyl radical scavenging capacity.

Experimentation Series 1

Water samples from four water treatment plants (WTPs I, II, III and IV) were obtained and their scavenging capacity was monitored. For some of these water samples, the measurement was conducted using different methods, including methods, A, B and C.

Method A generally corresponds to a method employed by Xylem Water Solutions Herford GmbH (also referred to as the "Xylem method" herein). Method B corresponds to the Trojan method. It uses other organic matter as the probe compound, such as para-chlorobenzoic acid, and involves analytical techniques such as chromatographic separation. Method B is considered accurate and can be used as a quality check measure, but is not suitable for online-monitoring. Method C corresponds to an embodiment of the invention described herein using external calibration.

Table 1 compares the scavenging capacity of the samples measured by methods A, B and C. It was apparent that method A had difficulty in achieving results consistent with those achieved using method B (see FIG. 4). As previously explained, method A involves heavy mathematical calculations and is subject to several sources of errors such as the UV intensity measurement and the dye concentration measurement.

TABLE 1

Comparison of the radical scavenging capacity ($s^{-1}$) measured using the methods A, B and C

| Sample # | Sample ID | Method A | Method C | Method B |
|---|---|---|---|---|
| 1 | WTP IV, sample 1 | 12.5 | 5.3 | 5.4 |
| 2 | WTP IV, sample 4 | 9.3 | 7.4 | 7.3 |
| 3 | WTP IV, sample 5 | 9.0 | 8.1 | 7.3 |
| 4 | WTP I, sample 1 | 5.9 | / | 4.1 |
| 5 | WTP I, sample 2 | 5.0 | / | 9.4 |
| 6 | WTP II, sample 1 | 4.5 | / | 7.3 |
| 7 | WTP III, sample 1 | 4.1 | / | 6.1 |
| 8 | WTP II, sample 2 | 3.7 | / | 10.7 |
| 9 | WTP III, sample 2 | 3.6 | / | 11.8 |
| 10 | WTP IV, sample 6 | / | 4.7 | 4.3 |

Note:
(1) "/" means data is not available;
(2) the theory behind method A is the same as that behind the Xylem method, although the devices used were somewhat different.

Figure 4:
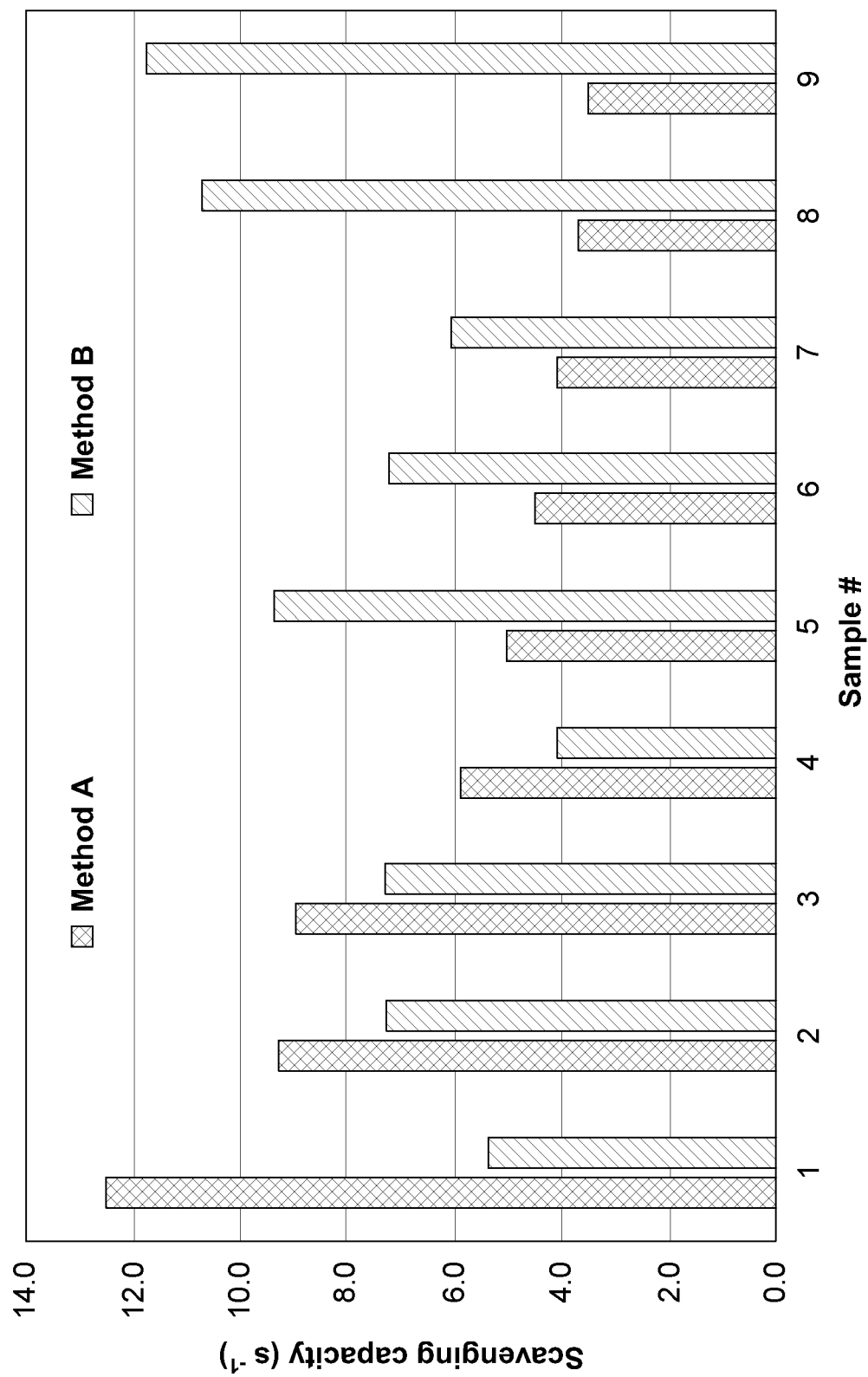
FIG. 4 is a graph of scavenging capacity versus sample number determined using two methods A and B for determining radical scavenging capacity of different samples.
Figure 5:
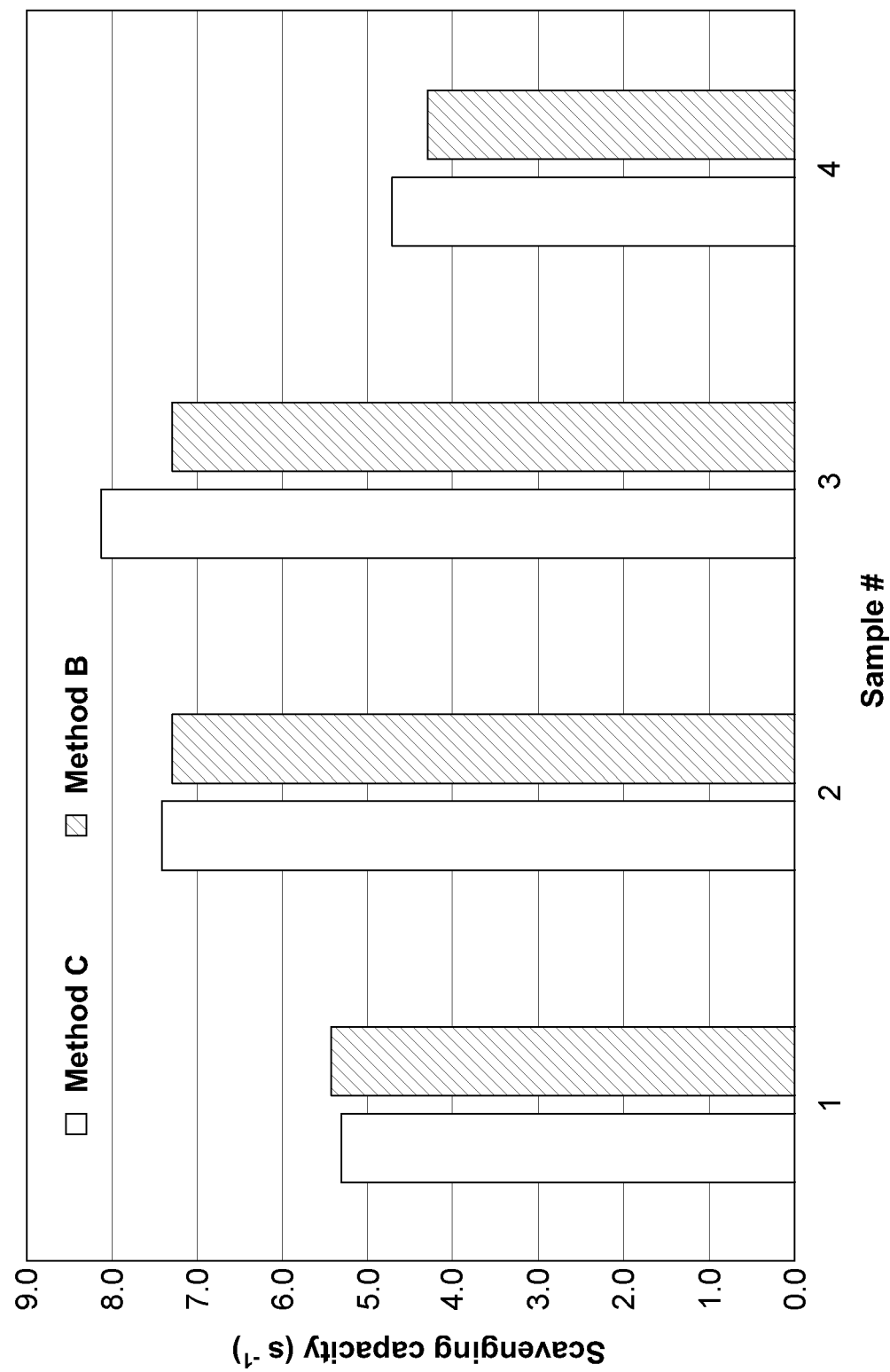
FIG. 5 is a graph of scavenging capacity versus sample number determined using two methods B and C for determining radical scavenging capacity of different samples.

FIG. 4 shows that method A was not able to provide consistently accurate results compared to the reference method B. FIG. 5 shows that method C was able to provide consistent results that aligned with the results of method B, which supports the finding of enhanced accuracy of method C. FIG. 5 shows that the difference between these two sets of results was negligible (<10%), and that compared with method B, method C is much simpler and can be used for online monitoring.

Experimentation Series 2

The following provides a more detailed and step-wise description of method C with certain explanations.

Step 1: Set up the system as in the following schematic graph. The pump speeds are fixed to make sure that the water flow (1), $H_2O_2$ flow (2), and dye flow (3) are constant. In addition, keep the UV intensity constant. See FIG. 1 which shows a schematic of the setup.

Step 2: Preparation of the standard solutions. IPA can be used where the solutions have different concentrations (e.g., 0 to 120 µM as in Table 2, which will cover most of the scavenging capacity values encountered in drinking water treatment). For each standard solution, determine its scavenging capacity, e.g., using a technique as described further above.

TABLE 2

| Standard # | IPA concentration (uM) | Scavenging capacity ($s^{-1}$) |
|---|---|---|
| 1 | 0 | 0 |
| 2 | 10 | $1.9 \times 10^4$ |
| 3 | 20 | $3.8 \times 10^4$ |
| 4 | 40 | $7.6 \times 10^4$ |
| 5 | 60 | $11.4 \times 10^4$ |
| 6 | 80 | $15.2 \times 10^4$ |
| 7 | 100 | $19.0 \times 10^4$ |
| 8 | 120 | $22.8 \times 10^4$ |

As this method relies on external calibration, a stable and accurate external standard solution is important. The use of alcohols is suggested for reasons explained above.

Step 3: Pump standard solution #1 through the system and record the absorbance at the signature wavelength of the dye (e.g., 600 nm for methylene blue). See FIG. 1 where the detector is configured to measure absorbance of the treated standard solution #1 after the UV treatment. The absorbance of standard solution #1 would be measured and recorded. After standard solution #1 has been assessed, then switch to standard solution #2, repeat the process, and record the absorbance reading. Then repeat with standard solutions #3, #4, #5, #6, #7, and #8, recording the absorbance reading for each case.

Step 4: Establish the external calibration model, e.g., as a curve of scavenging capacity vs the adsorption reading.

Step 5: Switch the sampling line to the water source or pipeline in the AOP plant and start the online monitoring. Keep all variables, including pump speeds, the same as in Step 3. See FIG. 2 for the setup coupled to the water pipeline in the AOP plant, so as to withdraw a slipstream of the contaminated water through the sample line.

Step 6: For the slipstream, record the absorbance reading at the signature wavelength of the dye.

Step 7: Using the external calibration model, convert the absorbance reading of the slipstream to scavenging capacity. This determination of scavenging capacity cab be done in various ways by referring to the standard curve established in Step 5. This can be done using a software.

Note that this method and system can provide accurate determination of scavenging capacities for an advanced oxidation system particularly when the contaminated water itself has negligible or no absorption at the dye's signature wavelength.

Note that the setup shown in FIGS. 1 and 2 can be adapted for cases where the contaminated water has absorption at the dye's wavelength. If the contaminated water itself (i.e., water without the dye) presents absorption at the dye's signature wavelength sufficient to pose an interference risk on the absorbance reading of the dye after the UV treatment, a second detector can be installed to correct this interference. FIG. 3 shows a setup with an additional detector for obtaining an absorbance reading prior to UV treatment and radical formation. The additional detector measures the adsorption of the influent contaminated water. Furthermore, the calibration curve can be established not as scavenging capacity vs the absorption reading, but as scavenging capacity vs $1/\Delta_{ln(absorbance)}$ (see FIG. 3). As the absorption in the raw water usually exists in both the influent and effluent and it can thus be substantially eliminated by adopting $\Delta_{absorbance}$ (i.e., the difference of the absorbance in the influent and effluent). For the calibration, one can use $1/\Delta_{absorbance}$ instead of $\Delta_{absorbance}$ because scavenging capacity versus $1/\Delta_{ln(absorbance)}$ tends to generate a linear calibration curve while the scavenging capacity vs $\Delta_{absorbance}$ would not. This can be proved mathematically. An example of a linear calibration curve is provided in FIG. 9 (acquired at $H_2O_2$ concentration of 25 mg/L and MB concentration of 5 µM over standard IPA solutions of 1 to 120 µM).

The invention claimed is:

1. A process for treating contaminated water using an advanced oxidation process (AOP) that includes addition of hydrogen peroxide and ultraviolet (UV) treatment to generate hydroxyl radicals, the process comprising:
   withdrawing a slipstream of the contaminated water upstream of the addition of the hydrogen peroxide and the UV treatment;
   determining hydroxyl radical scavenging capacity of the slipstream, comprising:
      adding hydrogen peroxide and a dye to the slipstream;
      subjecting the slipstream to a UV treatment to generate hydroxyl radicals that react with contaminants and the dye in the slipstream, to produce a treated slipstream;
      determining absorbance of the treated slipstream at a signature wavelength of the dye to obtain an absorbance measurement; and
      converting the absorbance measurement to hydroxyl radical scavenging capacity via a pre-determined external calibration model and thereby determining the hydroxyl radical scavenging capacity of the contaminated water from which the slipstream was withdrawn, wherein the external calibration model has been developed by:
         preparing multiple standard solutions comprising water and an alcohol scavenger compound at different concentrations;
         determining respective hydroxyl radical scavenging capacities of the standard solutions;
         adding to each standard solution hydrogen peroxide and a dye of the same type as added to the slipstream;
         subjecting each standard solution to UV treatment to generate hydroxyl radicals that react with the dye and the alcohol scavenger compound, to partially degrade the dye such that a resulting treated standard solution has a corresponding residual dye content; and
         determining absorbance at the signature wavelength of the dye of each treated standard solution to obtain a corresponding absorbance measurement, and to thereby obtain a relation between hydroxyl radical scavenging capacity and the absorbance measurement to provide the external calibration model; and controlling the AOP based on the determined hydroxyl radical scavenging capacity of the contaminated water.

2. The process of claim 1, wherein the dye is methylene blue (MB).

3. The process of claim 2, wherein the MB is provided at an MB concentration between 1 µM and 10 µM in the slipstream and in the standard solutions.

4. The process of claim 1, wherein the alcohol scavenger compound is isopropyl alcohol (IPA).

5. The process of claim 4, wherein the IPA is provided in IPA concentrations between 0 µM and 120 µM in the standard solutions.

6. The process of claim 1, wherein the UV treatment comprises subjecting the standard solutions and the slipstream to a fixed UV intensity over a fixed time.

7. The process of claim 1, wherein the external calibration model comprises a calibration curve of $1/\Delta_{ln(absorbance)}$ versus scavenging capacity where absorbance readings are taken before and after the UV treatment; absorbance versus scavenging capacity; 1/absorbance versus scavenging capacity; or Δabsorbance versus scavenging capacity where absorbance readings are taken before and after the UV treatment.

8. A process for treating contaminated water using an advanced oxidation process (AOP) that includes addition of a primary oxidant or oxidant generator and ultraviolet (UV) treatment to generate hydroxyl radicals, the process comprising:
obtaining a sample of the contaminated water upstream of the addition of the primary oxidant and the UV treatment;
determining hydroxyl radical scavenging capacity of the sample, comprising:
adding an oxidant and an indicator to the sample;
subjecting the sample to a UV treatment to generate hydroxyl radicals that react with contaminants and the indicator in the sample, to produce a treated sample;
determining a residual indicator content parameter of the treated sample; and
converting the residual indicator content parameter to hydroxyl radical scavenging capacity via a predetermined external calibration model and thereby determining the hydroxyl radical scavenging capacity of the contaminated water from which the sample was obtained, wherein the external calibration model has been developed by:
preparing multiple standard solutions comprising water and a scavenger compound at different concentrations;
determining respective hydroxyl radical scavenging capacities of the standard solutions;
adding to each standard solution an oxidant of the same type as added to the sample, and an indicator of the same type as added to the sample;
subjecting each standard solution to UV treatment to generate hydroxyl radicals that react with the indicator and the scavenger compound to partially degrade the indicator such that a resulting treated standard solution has a corresponding residual indicator content; and
determining a residual indicator content parameter of each treated standard solution, to thereby obtain a relation between hydroxyl radical scavenging capacity and the residual indicator content to provide the external calibration model; and controlling the AOP based on the determined hydroxyl radical scavenging capacity of the contaminated water.

9. The process of claim 8, wherein the sample of the contaminated water is a slipstream; the primary oxidant of the AOP is hydrogen peroxide; the oxidant in determining the hydroxyl radical scavenging capacity of the sample is hydrogen peroxide; the oxidant in determining respective hydroxyl radical scavenging capacities of the standard solutions is hydrogen peroxide; the indicator is a dye; and the contaminated water is contaminated drinking water.

10. The process of claim 8, wherein the steps of determining the residual indicator content parameter of the treated sample and determining the residual indicator content parameter of the corresponding standard solutions, comprises determining absorbance at the signature wavelength of the indicator, to obtain a relation between hydroxyl radical scavenging capacity and the absorbance measurement to provide the external calibration model.

11. The process of claim 10, wherein the external calibration model comprises a calibration curve of $1/\Delta_{ln(absorbance)}$ versus scavenging capacity where absorbance readings are taken before and after the UV treatment; absorbance versus scavenging capacity; 1/absorbance versus scavenging capacity; or Δabsorbance versus scavenging capacity where absorbance readings are taken before and after the UV treatment.

12. The process of claim 8, wherein the scavenger compound is an alcohol scavenger compound.

13. The process of claim 12, wherein the alcohol scavenger compound is isopropyl alcohol (IPA) or tert butyl alcohol (TBA).

14. The process of claim 8, wherein the UV treatment comprises providing a plug flow of the sample that includes the hydrogen peroxide and the dye through a UV-transparent pipe within a UV cell, and exposing the plug flow to UV light at the fixed UV intensity over a fixed time while travelling through the UV-transparent pipe.

15. A method for treating contaminated water using an advanced oxidation process (AOP), comprising:
obtaining a water sample from contaminated water in an AOP operation;
determining hydroxyl radical scavenging capacity of the water sample using an external calibration model; and
controlling at least one unit operation of the AOP based on the determined hydroxyl radical scavenging capacity of the water sample;
wherein determining hydroxyl radical scavenging capacity of the water sample comprises performing a monitoring protocol on the water sample, wherein the monitoring protocol is substantially the same as a calibration protocol performed on standard solutions to develop the external calibration model; and
wherein the calibration protocol comprises:
preparing multiple standard solutions comprising water and a scavenger compound at different concentrations;
determining respective hydroxyl radical scavenging capacities of the standard solutions;
adding to each standard solution an indicator;
subjecting each standard solution to an oxidation process, to generate hydroxyl radicals that react with the indicator and the scavenger compound to partially degrade the indicator such that a resulting treated standard solution has a corresponding residual indicator content; and determining a residual indicator content parameter of each treated standard solution, to thereby obtain a relation between hydroxyl radical scavenging capacity and the residual indicator content to provide the external calibration model.

16. The method of claim 15, wherein the monitoring protocol comprises:

adding an indicator to the sample that is the same as added to the standard solutions;

subjecting the sample to an oxidation process that is the same as added to the standard solutions, to generate hydroxyl radicals that react with contaminants and the indicator in the sample, to produce a treated sample;

determining a residual indicator content parameter of the treated sample; and converting the residual indicator content parameter to hydroxyl radical scavenging capacity via the external calibration model and thereby determining the hydroxyl radical scavenging capacity of the water sample.

17. The method of claim 16, wherein the monitoring protocol further comprises:

determining an interference value of the water sample prior to the oxidation process;

determining the residual indicator content parameter by factoring in the interference value; and wherein the interference value is absorbance at the signature wavelength of the indicator, and is determined by obtaining an initial absorbance measurement of the water sample prior to the oxidation.

18. The method of claim 17, wherein the external calibration model comprises a relation between scavenging capacity and $1/\Delta_{ln(absorbance)}$ wherein $\Delta_{ln(absorbance)}$ is the difference between (i) natural logarithm of the initial absorbance measurement of the water sample prior to the oxidation process and (ii) the natural logarithm of an absorbance measurement of the treated sample after the oxidation process.

19. The method of claim 18, wherein the external calibration model comprises a linear relation of scavenging capacity versus $1/\Delta_{ln(absorbance)}$.

* * * * *